(12) United States Patent
Lee et al.

(10) Patent No.: US 11,877,735 B2
(45) Date of Patent: Jan. 23, 2024

(54) TISSUE RETRACTION DEVICE AND DELIVERY SYSTEM

(71) Applicant: BOSTON SCIENTIFIC SCIMED, INC., Maple Grove, MN (US)

(72) Inventors: Danny Shu-Huan Lee, Framingham, MA (US); Paul Smith, Smithfield, RI (US); Ryan V. Wales, Northborough, MA (US); Jialiang Wang, Smithfield, RI (US); Niklas Andersson, Wayland, MA (US); Gregory Hurley, Windham, NH (US); Jon Taylor, Groton, MA (US); John Unger, Wrentham, MA (US); Irina Pyataeva, Moscow (RU)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 58 days.

(21) Appl. No.: 17/397,087

(22) Filed: Aug. 9, 2021

(65) Prior Publication Data
US 2022/0000466 A1 Jan. 6, 2022

Related U.S. Application Data

(62) Division of application No. 15/925,110, filed on Mar. 19, 2018, now Pat. No. 11,109,850.

(Continued)

(51) Int. Cl.
*A61B 17/02* (2006.01)
*A61B 17/00* (2006.01)
(Continued)

(52) U.S. Cl.
CPC ...... *A61B 17/0206* (2013.01); *A61B 17/0218* (2013.01); *A61B 1/018* (2013.01); *A61B 1/32* (2013.01); *A61B 17/1227* (2013.01); *A61B 2017/00004* (2013.01); *A61B 2017/00778* (2013.01); *A61B 2017/00818* (2013.01); *A61B 2017/00862* (2013.01);
(Continued)

(58) Field of Classification Search
CPC ............ A61B 17/0206; A61B 17/0218
See application file for complete search history.

(56) References Cited

U.S. PATENT DOCUMENTS

2002/0156454 A1  10/2002  Reydel
2005/0043580 A1*  2/2005  Watschke ......... A61B 17/06109
                                            600/30
2012/0078057 A1  3/2012  Scott

FOREIGN PATENT DOCUMENTS

CN          101991441 A     3/2011

* cited by examiner

*Primary Examiner* — Olivia C Chang
(74) *Attorney, Agent, or Firm* — Seager, Tufte & Wickhem, LLP

(57) ABSTRACT

Medical devices and methods of using medical devices are disclosed. An example tissue retraction device includes a first engagement member having a first end and a second end, a second engagement member having a first end and a second end, a first elastic member attached to the second end of the first engagement member, and a first alignment member having a first end, a second end and a lumen extending therethrough. Further, the tissue retraction device has a first length, the first alignment member has a second length, the first elastic member extends within the lumen of the first alignment member and the second length of the first alignment member is less than or equal to the first length of the tissue retraction device.

20 Claims, 41 Drawing Sheets

Related U.S. Application Data

(60) Provisional application No. 62/506,780, filed on May 16, 2017, provisional application No. 62/473,957, filed on Mar. 20, 2017.

(51) Int. Cl.
  *A61B 1/32* (2006.01)
  *A61B 90/00* (2016.01)
  *A61B 1/018* (2006.01)
  *A61B 17/122* (2006.01)

(52) U.S. Cl.
  CPC . *A61B 2017/0287* (2013.01); *A61B 2090/061* (2016.02); *A61B 2090/0807* (2016.02)

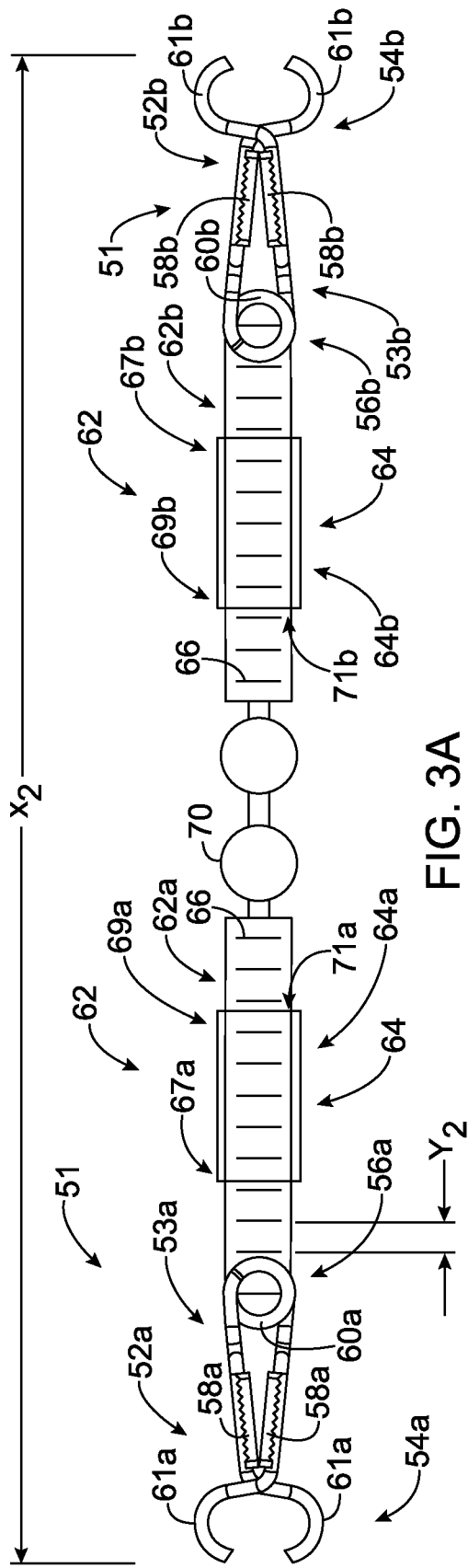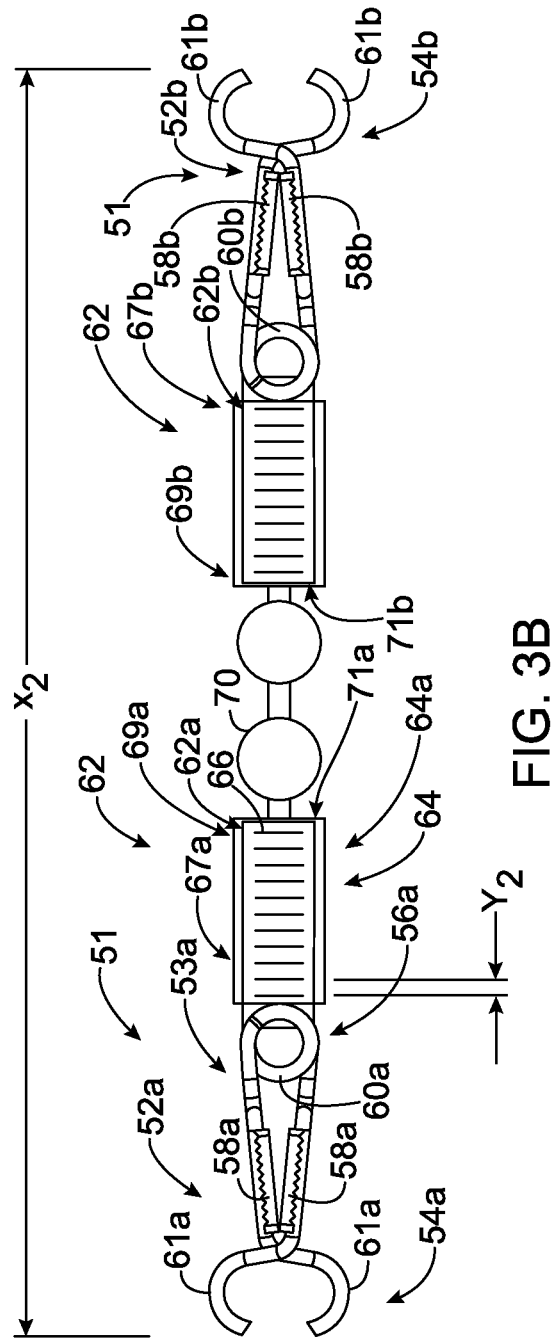

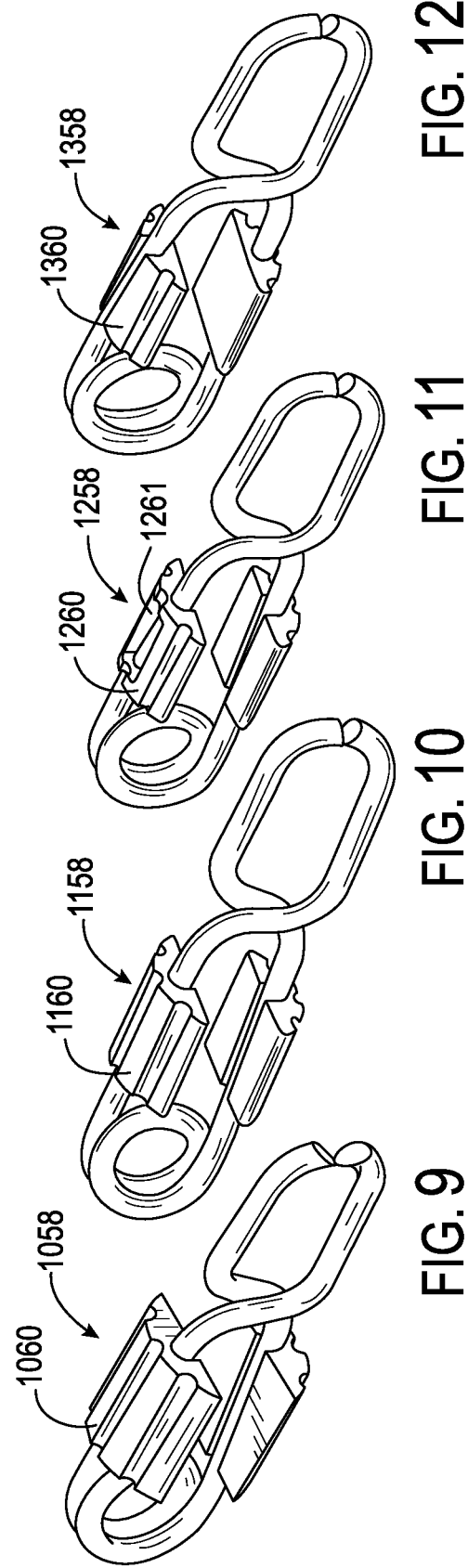

TISSUE RETRACTION DEVICE AND DELIVERY SYSTEM

CROSS-REFERENCE TO RELATED APPLICATIONS

This application is a divisional of and claims the benefit of the earlier filing date of U.S. application Ser. No. 15/925,110, filed Mar. 19, 2018, which application claims priority under 35 U.S.C. § 119 to U.S. Provisional Application Ser. No. 62/473,957, filed Mar. 20, 2017, and claims priority under 35 U.S.C. § 119 to U.S. Provisional Application Ser. No. 62/506,780, filed May 16, 2017, the entirety of which applications are incorporated herein by reference for all purposes.

TECHNICAL FIELD

The present disclosure pertains to medical devices, and methods for manufacturing medical devices. More particularly, the present disclosure pertains to a tissue retraction device and related delivery system.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example tissue retraction device includes a first engagement member having a first end and a second end; a second engagement member having a first end and a second end; a first elastic member disposed between the first and second engagement members; and a first alignment member having a first end, a second end and a lumen extending therethrough. The tissue retraction device has a first length, and the first alignment member has a second length. The first elastic member extends within the lumen of the first alignment member; and the second length of the first alignment member is less than or equal to the first length of the tissue retraction device.

Alternatively or additionally to any of the embodiments above, wherein the elastic member is designed to shift from a first position to a second elongated position.

Alternatively or additionally to any of the embodiments above, wherein the elastic member further includes a plurality of markers, wherein the markers are designed to indicate when the degree of elongation of the elastic member.

Alternatively or additionally to any of the embodiments above, wherein the alignment member is designed to keep the elastic member from folding.

Alternatively or additionally to any of the embodiments above, wherein the elastic member includes at least one recessed portion and wherein the alignment member is disposed along the recessed portion.

Alternatively or additionally to any of the embodiments above, wherein the alignment member is tubular.

Alternatively or additionally to any of the embodiments above, wherein the first engagement member further includes a pair of gripping members.

Alternatively or additionally to any of the embodiments above, further comprising a second elastic member disposed between the first and the second engagement members.

Alternatively or additionally to any of the embodiments above, further comprising a second alignment member having a first end, a second end and a lumen extending therethrough, wherein the second elastic member extends within the lumen of the second alignment member from the first end of the alignment member to the second end of the alignment member.

Alternatively or additionally to any of the embodiments above, further comprising a swivel, wherein the swivel is coupled to both the first elastic member and the second elastic member.

Alternatively or additionally to any of the embodiments above, wherein the swivel is designed to permit the first engagement member to rotate relative to the second engagement member.

Another example is a tissue retraction device including a first engagement member having a first end and a second end; a second engagement member having a first end and a second end; a first elastic member disposed between the first engagement member and the second engagement member; and a first swivel disposed between the first engagement member and the second engagement member.

Alternatively or additionally to any of the embodiments above, wherein a first end of the elastic member is coupled to the first swivel, and wherein a second end of the elastic member is coupled to the second end of the first engagement member.

Alternatively or additionally to any of the embodiments above, further comprising a second swivel disposed between the first engagement member and the second engagement member, wherein the first swivel is positioned between the first engagement member and the first elastic member, and wherein the second swivel is positioned between the second engagement member and the first elastic member.

Alternatively or additionally to any of the embodiments above, wherein the first elastic member includes a plurality of markers, wherein the markers are designed to indicate the degree of elongation of the first elastic member.

Alternatively or additionally to any of the embodiments above, wherein the first engagement member and the second engagement member each include a pair of gripping members coupled thereto.

Alternatively or additionally to any of the embodiments above, further comprising a second elastic member and wherein the swivel is positioned between the first and second engagement members.

Alternatively or additionally to any of the embodiments above, wherein the first alignment member and the second alignment member are tubular.

Another example is a tissue retraction system including a tissue retraction device, wherein the tissue retraction device includes: a first engagement member having a first end and a second end; a second engagement member having a first end and a second end; a first elastic member attached to the second end of the first engagement member; and a first alignment member having a first end, a second end and a lumen extending therethrough. The first elastic member extends within the lumen of the first alignment member. The system may include a delivery catheter including a distal end, a proximal end and a lumen extending therein; wherein the tissue retraction device is positioned within the lumen of the delivery catheter prior to being deployed in a body lumen.

Alternatively or additionally to any of the embodiments above, further comprising a manipulator positioned in the lumen of the delivery catheter.

Another example tissue retraction device includes a first engagement member having a first tissue engagement portion and a first actuation portion, a second engagement member having a second tissue engagement portion and a second actuation portion, a first elastic member disposed between the first and second engagement members, and a first interface member coupled to the first actuation portion of the first engagement member. Further, manipulation of the first interface member actuates the first tissue engagement portion between a first configuration and a second open configuration.

Alternatively or additionally to any of the embodiments above, wherein the first tissue engagement portion is adjacent to the first actuation portion, and wherein the second tissue engagement portion is adjacent to the second actuation portion.

Alternatively or additionally to any of the embodiments above, wherein the first elastic member includes a first end coupled to the first engagement member and a second end coupled to the second engagement member.

Alternatively or additionally to any of the embodiments above, wherein the elastic member is designed to shift from a first position to a second elongated position.

Alternatively or additionally to any of the embodiments above, wherein the interface member is configured to engage with a pull-back member.

Alternatively or additionally to any of the embodiments above, wherein the pull-back member extends within a lumen of a support catheter.

Alternatively or additionally to any of the embodiments above, wherein the pull-back member, the support catheter and the tissue retraction device are configured to be delivered to a target site while positioned inside a deployment catheter.

Alternatively or additionally to any of the embodiments above, wherein the support catheter is designed to push the tissue retraction member out of a distal end of the deployment catheter, and wherein the pull-back member remains engaged with the interface member after the tissue retraction member is pushed out of the distal end of the deployment catheter.

Alternatively or additionally to any of the embodiments above, wherein the pull-back member is configured to retract the interface member within the lumen of the support catheter.

Alternatively or additionally to any of the embodiments above, wherein retraction of the interface member into the lumen of the support catheter draws the first engagement member into contact with a distal end region of the support catheter, and wherein contact of the first engagement member with the support member actuates the first tissue engagement portion from the first configuration to the second open configuration.

Alternatively or additionally to any of the embodiments above, wherein interface member includes a flexible strap.

Alternatively or additionally to any of the embodiments above, wherein the interface member includes an arcuate portion.

Alternatively or additionally to any of the embodiments above, wherein the interface member includes a wire.

Another example tissue retraction system includes:
a deployment catheter including a proximal end, a distal end and a lumen extending therein;
a support catheter slidably disposed within the lumen of a deployment catheter;
a pull-back member including a proximal end region and a distal end region, the pull-back member translatable within the lumen of the support catheter; and
a first tissue engagement member including an interface member, wherein the interface member is engaged with the distal end region of the pull-back member;
wherein the pull-back member is configured to withdraw the interface member proximally into the lumen of the support member, and wherein withdrawing the interface member proximally into the lumen of the support member actuates a portion of the first tissue engagement member between a first configuration and a second open configuration.

Alternatively or additionally to any of the embodiments above, further comprising an elastic member coupled to the first tissue engagement member.

Alternatively or additionally to any of the embodiments above, wherein the elastic member includes a first end coupled to the first tissue engagement member and a second end coupled to a second engagement member.

Alternatively or additionally to any of the embodiments above, wherein the elastic member is designed to shift from a first position to a second elongated position.

Alternatively or additionally to any of the embodiments above, wherein interface member includes a flexible strap.

Alternatively or additionally to any of the embodiments above, wherein the interface member includes a wire.

An example method of dissecting tissue includes:
advancing a tissue retraction device to a target site, the tissue retraction device including:
a first engagement member having a first tissue engagement portion and a
first actuation portion;
a first elastic member coupled to the first engagement member; and
a first interface member coupled to the first actuation portion of the first engagement member;
manipulating the first interface member to actuate the first tissue engagement portion between a first configuration and a second open configuration; and
attaching the first tissue engagement portion to the target site.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 3A is a plan view of another example tissue retraction device;

FIG. 3B is a plan view of the example tissue retraction device illustrated in FIG. 3A in an example of a storage configuration;

FIGS. 4-12 illustrate example gripping members utilized with example tissue retraction devices;

Figure 1:
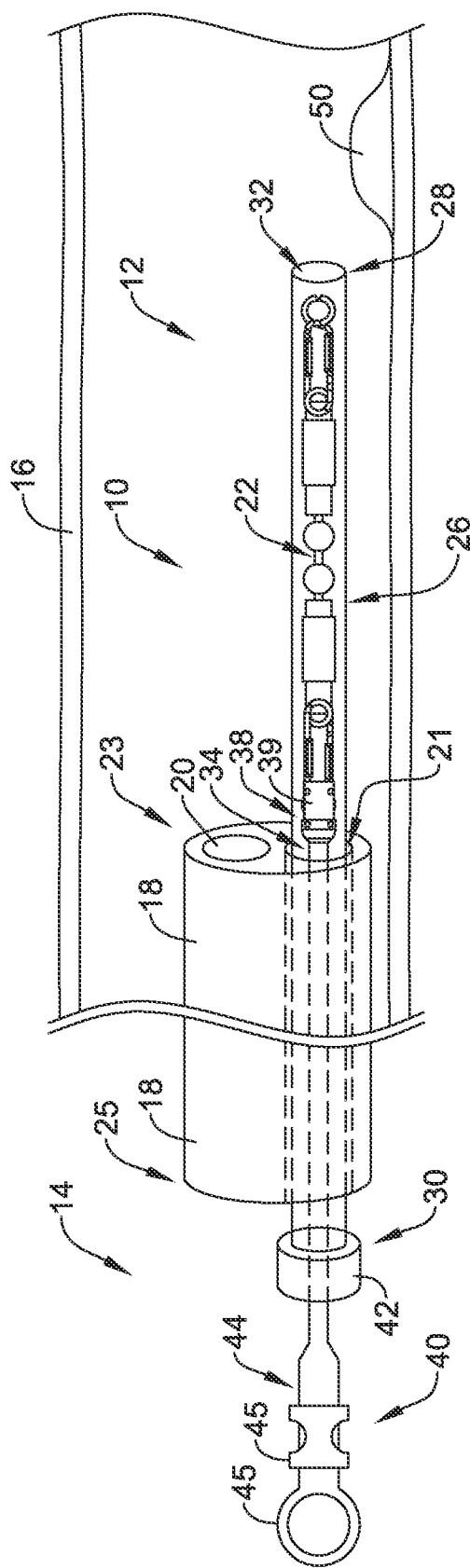
FIG. 1 is a partial cross-sectional side view of an example tissue retraction device positioned within a body lumen.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, including intravascular procedures, procedures along the digestive and/or biliary tract, thoracic procedures, etc. utilize medical devices to access tissue intended for removal (e.g., "target tissue") within the body. For example, in some current medical procedures (e.g., Endoscopic Submucosal Dissection (ESD), Peroral Endoscopic Myotomy (POEM), cholecystectomy, Video-Assisted Thoracoscopic Surgery (VATS)), physicians may utilize an endoscope or similar medical device to access and remove cancerous lesions. Further, as part of the procedure, the physician may utilize an endoscope capable of both accessing the target tissue site while also permitting a cutting device to be deployed therethrough to excise the target tissue. Additionally, in some instances, the endoscope may incorporate features which assist the physician in visualizing and performing the tissue dissection procedure. For example, some endoscopes may include a light and/or camera designed to illuminate the body lumen as the scope is navigated and positioned adjacent to the target tissue site. Additionally, some endoscopes may also include a lumen (e.g., a working channel) through which a cutting member or other accessory medical devices may be deployed and utilized.

While physicians are becoming more proficient at extracting cancerous lesions from within the body (e.g., within the digestive tract, abdominal cavity, thoracic cavity, etc.), the extraction methods continue to be inefficient and time-consuming. For example, in some instances poor visualization of the tissue dissection process may result in a prolonged tissue dissection procedure. In another example, the actual tissue that the physician is attempting to dissect may, itself, obstruct the pathway of the tools which the physician is using during the procedure. Therefore, in some instances it may be desirable to utilize a medical device which assists in improving the visualization of the target tissue while also mitigating the obstruction of dissection tools the physician is utilizing. Therefore, in some instances it may be desirable to utilize a tissue retraction device which lifts and retracts the region of tissue to be dissected by the physician. Disclosed herein are medical devices such as a tissue retraction device and delivery system that are designed to lift and retract the target tissue.

FIG. 1 is a partial cross-sectional side view of an example tissue retraction delivery system 10 including a distal portion 12 and a proximal portion 14. FIG. 1 shows the distal portion 12 of the tissue retraction system 10 positioned within an example body lumen 16. Further, FIG. 1 shows that the proximal portion 14 of the tissue retraction system 10 may extend out of the body lumen 16 to a position outside the body. As shown in FIG. 1, the tissue retraction system may include a tissue retraction device 22. Additionally, the tissue retraction system 10 may include a delivery catheter 26. The delivery catheter 26 may be constructed from a semi-rigid or compliant material such as a thermoplastic elastomer, silicone rubber, nylon, polyurethane, polyethylene terephthalate (PET), latex, or similar materials. The delivery catheter 26 may have a distal end region 28 and a proximal end region 30. Further, a lumen 32 may extend through the delivery catheter 26 from proximal end region 30 to the distal end region 28. As illustrated, the tissue retraction device 22 may be positioned along the distal end region 28 and within the lumen 32 of the delivery catheter 26.

Additionally, FIG. 1 illustrates that the delivery catheter 26 (including the tissue retraction device 22) may extend through an example medical device 18. As discussed above, in FIG. 1 the medical device 18 may take the form of an endoscope, laproscope, needle, catheter, guide tube, or the like. The medical device 18 may include a distal portion 23 and a proximal portion 25. Further, FIG. 1 illustrates that the distal portion 23 of the medical device 18 may be advanced within a portion of a body lumen 16 to a position adjacent a target tissue 50, such as a lesion, while the proximal portion 25 of the medical device 18 may extend out of the body lumen 16 to a position outside the body.

Medical device 18 may include a lumen 21 extending from the proximal portion 25 to the distal portion 23 of the medical device 18. In some examples, the lumen 21 may be referred to as the "working channel" of the medical device 18. The lumen 21 may be designed to permit a variety of medical devices to pass therethrough. For example, a physician may pass or exchange a variety of medical devices through the working channel 21 over the course of a given medical procedure. For example, as illustrated in FIG. 1, the delivery catheter 26 (including the tissue retraction device 22) may extend through the lumen 21 of the medical device 18. In other words, FIG. 1 illustrates that a physician may insert the distal end 28 of the delivery catheter 26 into the proximal portion 25 of the medical device 18 (which is outside the body), advance the delivery catheter 26 through the lumen 21 whereby the distal end 28 of the delivery catheter may eventually extend out of the distal portion 23 of the medical device 18 to a position adjacent the target tissue 50.

The proximal end 30 of the delivery catheter 26 may include a control member 42. The control member 42 may be utilized as a grip to control the translation of the delivery catheter 26. Further, the control member 42 may also permit a user to rotate the delivery catheter 26. As will be described in greater detail below, the control member 42 may be utilized by a physician to advance the distal end 28 of the delivery catheter 26 to a position adjacent a target tissue 50 prior to deploying the tissue retraction device 22 from the distal end 28 of the delivery catheter 26.

In some examples, the medical device 18 may include additional features. For example, the medical device 18 shown in FIG. 1 may include an accessory feature 20 (e.g., light, camera, etc.) positioned on the distal portion 23 of the medical device 18. Further, other medical devices 18 having additional features may be utilized in conjunction with the tissue retraction system 10.

As illustrated in FIG. 1, in some examples the tissue retraction system 10 may include a manipulating device 34 ("manipulator") designed to advance (e.g., push, deploy, etc.) the tissue retraction device 22 out of the distal end 28 of the delivery catheter 26. As will be described in greater detail below, once the manipulator 34 has pushed the tissue retraction device 22 out of the delivery catheter 26, it may also be used to position and/or manipulate the tissue retraction device 22 within the body lumen 16.

As shown in FIG. 1, the manipulator 34 may extend within the lumen 32 of the delivery catheter 26. In other words, FIG. 1 illustrates that a distal end 38 of the manipulator 34 may extend from the proximal end 30 of the delivery catheter 26 (which is outside the body), through the lumen 32 of the delivery catheter 26 whereby the distal end 38 of the manipulator 34 may be positioned adjacent the proximal end of the tissue retraction device 22.

The proximal end 40 of the manipulator 34 may include a handle member 44. Handle member 44 may include one or more finger grips 45 which permit a user to grasp and thereby advance (e.g., translate) the distal end 38 of the manipulator within the lumen 32 of the delivery catheter 26. In other words, by grasping and manipulating the handle 44, a user may be able to translate the manipulator 34 along the longitudinal axis of the delivery catheter 26. The handle design illustrated in FIG. 1 is a schematic. Other handle designs are contemplated. For example, handle designs that include different grip arrangements, ergonomic features, etc. that may be utilized with the tissue retraction system 10 (and components thereof) described herein are contemplated.

The distal end 38 of the manipulator 34 may include a grasping member 39 (e.g., forceps, jaws, etc.). When positioned within the lumen 32 of the delivery catheter 26, the grasping member 39 may be in a closed position (e.g., the jaws of the grasping member 39 may be closed and contacting one another). Further, the handle member 44 may be designed to control the opening and/or closing of the grasping member 39. In other words, when the grasping member 39 is advanced to a position outside of the lumen 32 of the delivery catheter 26, a user may manipulate the handle member 44 to open and/or close the grasping member 39.

As described above, the manipulator 34 may be utilized to deploy the tissue retraction device 22 out of the distal end 28 of the delivery catheter 26. Specifically, it can be appreciated that, when positioned adjacent to tissue target 50, a user may advance the manipulator 34 in a proximal-to-distal direction within the lumen 32 of the delivery catheter 26 such that the grasping member 39 may contact and push the proximal end of the tissue retraction device 22 out of the distal end 28 of the delivery catheter 26.

In at least some examples contemplated herein, the manipulator 34 and the tissue retraction device 22 may be positioned within the delivery catheter 26 as depicted in FIG. 1 prior to the delivery catheter 26 being advanced through the lumen 21 of the medical device 18. In other words, in some examples, both the manipulator 34 and the tissue retraction device 22 may be "pre-loaded" into the delivery catheter 26 prior to being inserted and advanced through the working channel 21 of the medical device 18 to a position adjacent to target tissue 50. In other examples, however, only the tissue retraction device 22 may be pre-loaded into the delivery catheter 26 and advanced within the lumen 21 of the medical device 18 to a position adjacent to target tissue 50, after which the manipulator 34 may be separately inserted into the lumen 21 of the medical device 18 and advanced to a position in which grasping member 39 is adjacent and/or contacting the proximal end of the tissue retraction device 22.

It can be appreciated from the above discussion that tissue retraction system 10 may be designed such that the delivery catheter 26 and the manipulator 34 may be moved (e.g., translated, rotated, etc.) relative to one another. For example, once the distal end 28 of the delivery catheter 26 is positioned adjacent to the target tissue 50 (with the manipulator 34 positioned adjacent to the distal end of the tissue retraction device 22), a user may grasp both the control member 42 and the handle member 44. This may permit the user to maintain the distal end 28 of the delivery catheter 26 in a fixed position while advancing the manipulator in a distal direction such that the grasping member 39 moves distally relative to the distal end 28 of the delivery catheter 26. It can be appreciated that this relative movement may push the tissue retraction device 22 out of the distal end 28 of the delivery catheter 26.

In other examples, it can be appreciated that instead of a user advancing the manipulator 34 in a distal direction to deploy the tissue retraction device 22, the user may, alternatively, retract the delivery catheter 26 while maintaining the manipulator 34 in a fixed position. The retraction of the delivery catheter 26 may "uncover" the tissue retraction device 22, thereby releasing it from the lumen 32 of the delivery catheter 26.

Figure 2A:
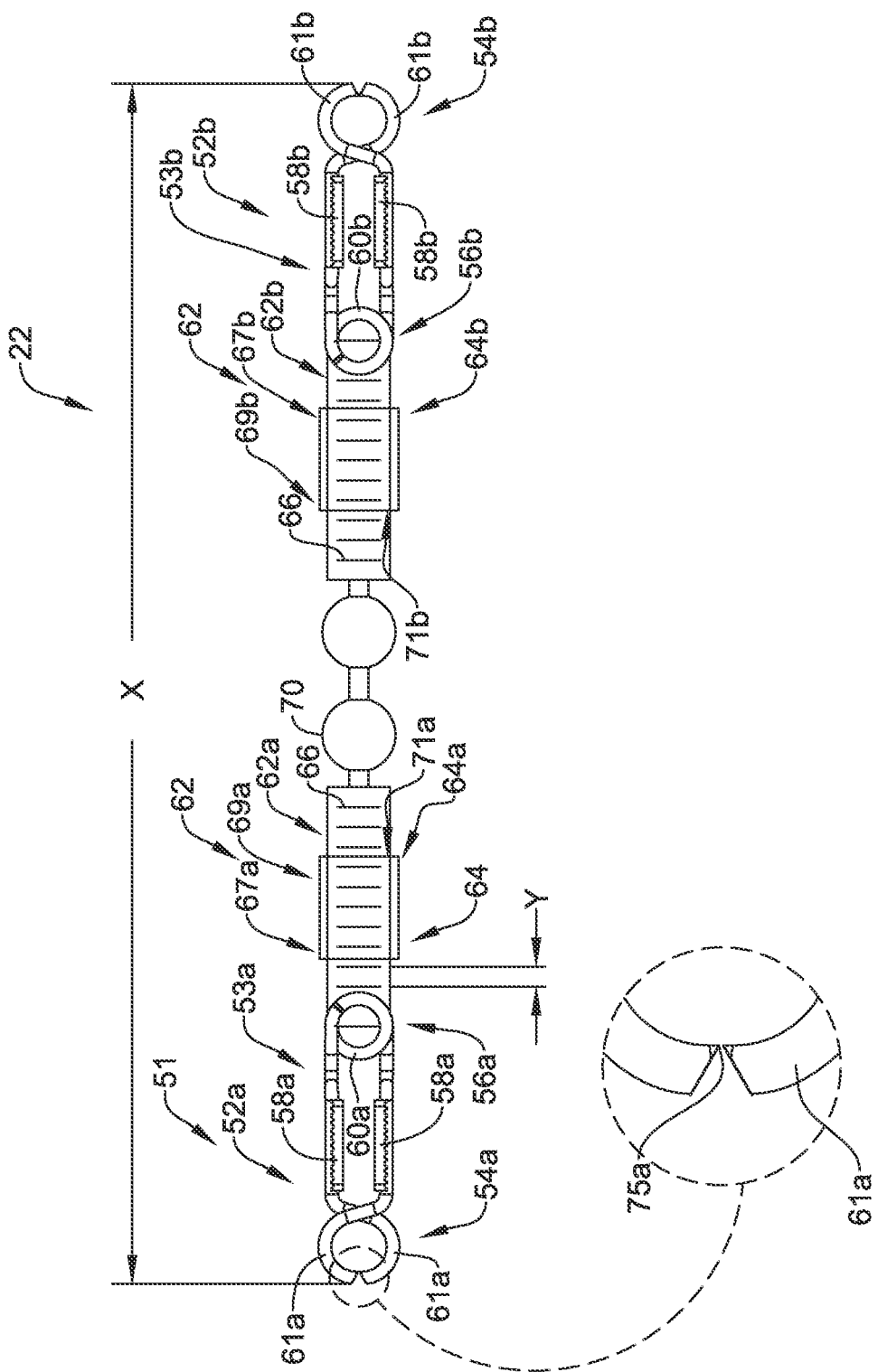
FIG. 2A is a plan view of an example tissue retraction device.

FIG. 2A illustrates an example tissue retraction device 22. The tissue retraction device 22 may include one or more engagement members 51 (e.g., clip, clasp, fastener, clamp, etc.). For example, FIG. 2A illustrates that the tissue retraction device 22 may include a first engagement member 52a and a second engagement member 52b. The first engagement member 52a may include a first end 54a, a second end 56a and a body portion 53a positioned between the first end 54a and the second end 56a. The first end 54a may include a one or more jaws 61a. As will be described further with respect to FIG. 3A, the jaws 61a may be designed such that they move relative to one another. FIG. 2A further illustrates that the second end 56a of the first engagement member 52a may include a spring element 60a. It can be appreciated that the spring element 60a may be designed to provide a compressive force that is translated through the body of the first engagement member 52a to the jaw members 61a, thereby biasing the jaw members 61a in a closed position (e.g., a position in which the jaw members 61a are contacting one another). However, the ends of the jaw members 61a may not necessarily contact one another while in a closed position. The jaw members 61a may be spaced apart from one another while in a closed position. Spacing the jaw members 61a apart from one another while in a closed position may permit additional compressive force to be generated when in contact with tissue. This additional compressive force could be termed "preload." The range of preload forces could vary from about 5 grams of force to about 200 grams of force, or about 15 grams of force to about 40 grams of force.

Furthermore, it can be appreciated that the jaw members 61a may be sharpened to exhibit a slope facing the second end 56a of the first engagement member 52a. For example, the detail view of FIG. 2A shows the slope creates a sharp point 75a that may engage tissue more aggressively. The direction of the slope enhances tissue engagement by discouraging captured tissue from disengaging. It can be appreciated that the engagement members 51 depicted in the examples disclosed herein are schematic. In other words, it is contemplated that the engagement members 51 described herein may include alternative design arrangements, features, geometries etc. without departing from the scope of the examples contemplated herein. For example, it is contemplated that the spring 60a of the first engagement member 52a may be positioned in the body 53a of the first engagement member 52a (in other words, the spring 60a may be positioned between the first end 54a and the second end 56a of the first engagement member 52a). Other variations are contemplated.

FIG. 2A further illustrates that the first engagement member 52a may include one or more gripping members 58a. As described above, after the tissue retraction device 22 has been deployed out of the distal end 28 of the delivery catheter 26, the manipulator 34 may be utilized to position and/or attach the tissue retraction device 22 to the target tissue 50 within body lumen 16. It can be appreciated that the gripping members 58a may be designed to engage the grasping member 39 (located on the distal end 38 of the manipulator 34). In other words, the gripping members 58a may provide an interface for which the grasping member 39 may engage, attach, grip, grab, capture, etc. the first engagement member 52a. Furthermore, the gripping members 58a may be designed such that they permit the manipulator 34 to efficiently acquire, position (and/or reposition), and open/close the jaws 61a of the first engagement member 52a. While FIG. 2A depicts the gripping members 58a located along the body portion 53a of the first engagement member 52a, it is contemplated that the gripping members 58a may be located along other portions of first engagement member 52a. For example, the gripping members 58a may be positioned on the first end 54a and/or the second end 56a of first engagement member 52a.

As discussed above, the tissue retraction device 22 may include more than one engagement member (e.g., another engagement member in addition to the first engagement member 52a described above). For example, FIG. 2A illustrates that the tissue retraction device 22 may include a second engagement member 52b. The second engagement member 52b may include a first end 54b, a second end 56b and a body portion 53b positioned between the first end 54b and the second end 56b. The first end 54b may include a one or more jaws 61b. As will be described further with respect to FIG. 3A, the jaws 61b may be designed such that they move relative to one another. FIG. 2A further illustrates that the second end 56b of the second engagement member 52b may include a spring element 60b. It can be appreciated that the spring element 60b may be designed to provide a compressive force that is translated through the body of the second engagement member 52b to the jaw members 61b, thereby biasing the jaw members 61b in a closed position (e.g., a position in which the jaw members 61b are contacting one another). It can be appreciated that the second engagement member 52b depicted in the examples disclosed herein is schematic. In other words, it is contemplated that the second engagement member 52b described herein may include alternative design arrangements, features, geometries, etc. without departing from the scope of the examples contemplated herein. For example, it is contemplated that the spring 60b of the second engagement member 52b may be positioned in the body 53b of the second engagement member 52b (in other words, the spring 60b may be positioned between the first end 54b and the second end 56b of the second engagement member 52b). Other variations are contemplated.

FIG. 2A further illustrates that the second engagement member 52b may include one or more gripping members 58b. As described above, after the tissue retraction device 22 has been deployed out of the distal end 28 of the delivery catheter 26, the manipulator 34 may be utilized to position and/or attach the tissue retraction device 22 to the target tissue 50 within body lumen 16. It can be appreciated that the gripping members 58b may be designed to engage the grasping member 39 (located on the distal end 38 of the manipulator 34). In other words, the gripping members 58b may provide an interface for which the grasping member 39 may engage, attach, grip, grab, capture, etc. the second engagement member 52b. Further, the gripping members 58b may be designed such that they permit the manipulator to efficiently acquire, position (and/or reposition), and open/close the jaws 61b of the second engagement member 52b. While FIG. 2A depicts the gripping members 58b located along the body portion 53b of the second engagement member 52b, it is contemplated that the gripping members 58b may be located along other portions of the second engagement member 52b. For example, the gripping members 58b may be positioned on the first end 54b and/or the second end 56b of the second engagement member 52b.

FIG. 2A further illustrates that the tissue retraction device 22 may include one or more tether members 62 coupled to the first engagement member 52a, the second engagement member 52b or both the first engagement member 52a and the second engagement member 52b. The tether 62 may be referred to as a band, rope, cord, leash, strap, strand, etc. The tether 62 may include a variety of cross-sectional geometries. For example, the tether may be circular, rectangular, triangular, or the like. Further, the tether 62 may be bioabsorbable.

Further, FIG. 2A illustrates a first tether member 62a coupled to the second end 56a of the first engagement member 52a and a second tether member 62b coupled to the second end 56b of the second engagement member 52b. In some examples, the tether members 62a/62b may be rigidly fixed to the second ends 60a/60b of each of the engagement members 52a/52b, respectively. Other designs are contemplated. For example, it is contemplated that tissue retraction device 22 may include a single tether 62 coupled to the first engagement member 52a and the second engagement member 52b.

FIG. 2A further illustrates that in some examples, the tissue retraction device 22 may include a swivel 70. As shown in FIG. 2A, the swivel 70 may be positioned between and coupled to the first tether 62a and the second tether 62b. It can be appreciated that the swivel 70 may be designed to permit the first engagement member 52a and first tether 62a to rotate relative to the second engagement member 52b and the second tether 62b. In other words, swivel 70 may permit the first engagement member 52a and first tether 62a to rotate independently around a central axis of the tissue retraction device 22 relative to the second engagement member 52b and the second tether 62b. The swivel 70 may be designed to provide complete rotation (e.g., 360 degree rotation) of the first engagement member 52a and first tether 62a relative to the second engagement member 52b and the second tether 62b. However, in other examples, swivel 70 may be designed provide only partial rotation (e.g., less than 360 degree rotation) of the first engagement member 52a and first tether 62a relative to the second engagement member 52b and the second tether 62b. It can be appreciated that the swivel 70 depicted in the examples disclosed herein is schematic. In other words, it is contemplated that the swivel 70 described herein may include alternative design arrangements, features, geometries etc. without departing from the scope of the examples contemplated herein. For example, it is contemplated that the swivel 70 may be incorporated into one or more of the tether members 62a/62b and/or the engagement members 52a/52b. As will be described below, it is contemplated that the tissue retraction system may include multiple swivels 70.

In at least some examples, the tether members 61a/61b may be elastomeric. In some examples, the tether members 62a/62b may be constructed from an elastomeric material such as latex, Nitrile® rubber, ethylene propylene diene rubber, silicone rubber, chloroprene, polychloroprene (e.g., Neoprene®), polyolefin, thermoplastic elastomer, polyisoprene, etc.

The tether members 62a/62b may elongate from a first, unelongated (e.g., relaxed) position to a second, elongated position. FIG. 2A and FIG. 3A depict the ability of the tissue retraction device 22 to elongate from a first, unelongated position to a second, elongated position. For example, FIG. 2A illustrates the tissue retraction device 22 has an overall length depicted as "X" in FIG. 2A when the tether members 62a/62b are in a relaxed, unelongated configuration. However, when one or more of the tether members 62 is elongated, the overall length of the tissue retraction device 22 elongates to an overall length depicted as "$X_2$" in FIG. 3A.

It can be appreciated that when the tissue retraction device 22 is in an elongated position (as shown in FIG. 3A), the tissue elongation device is in tension, and therefore includes a retraction force which is pulling the first engagement member 52a toward the second engagement member 52b along the longitudinal axis of the tissue retraction device 22. Furthermore, in some instances it may be desirable for a clinician to know the extent to which the tissue retraction device 22 has elongated (which may be proportional and indicative of the amount of tension that the tissue retraction device 22 is imparting to tissue and/or other body structures to which the engagement members 52a/52b are attached). Therefore, in some examples, the tether members 62a/62b may include a series of reference markers 66 designed to provide visual indicia of the amount of elongation of the first tether member 62a and/or the second tether member 62b.

For example, FIG. 2A illustrates the reference markers 66 spaced substantially equidistant from another along tether member 62a. The distance between adjacent reference markers 66 is depicted as "Y". It is contemplated that the same set of reference markers may be spaced the same distance along tether member 62b. Additionally, FIG. 3A illustrates that as tissue retraction device 22 elongates, the space between the reference markers 66 may lengthen, thereby indicating that the tether member on which they are located has elongated. For example, FIG. 3A shows the space between the reference markers as "$Y_2$" (wherein $Y_2$ is a greater value than Y). It can be appreciated that the reference markers 66 may provide a visual indication of the degree of both the elongation and/or retraction of the tissue retraction device 22. Further, the reference markers 66 may include a variety of markings, symbols, geometric patterns, colors, etc. For example, the markers 66 may include a series of alternating light and dark stripes equally spaced along the tether members 62a/62b. It is further contemplated that a clinician may be supplied with a chart that correlates that degree of separation of the reference markers to the degree of retraction force being generated by the tissue retraction device 22.

As described above, prior to being deployed from the delivery catheter 26, the tissue retraction device 22 may be positioned in an unelongated, relaxed state within the distal end 28 of the delivery catheter. Furthermore, proper alignment of the tissue retraction device 22 within the delivery catheter 26 (prior to deployment) must be maintained to ensure that the tissue retraction device 22 is efficiently deployed within the body lumen 16. For example, it is important to prevent the tissue retraction device 22 from folding and/or wrapping upon itself (e.g., folding back on itself) while being advanced and/or manipulated within the distal end 28 of the delivery catheter 26.

FIG. 2A illustrates that in some examples, the tissue retraction device 22 may include one or more alignment members 64. In some instances, alignment member 64 may be referred to as a sabot, fairing, scaffolding, separator, housing, cover, shell, splitting tube, or the like. For example, the tissue retraction device 22 may include a first alignment member 64a and second alignment member 64b. However, in other embodiments tissue retraction device may include single retraction member. As shown in FIG. 2A, first alignment member 64a may be a tubular member having a first end 67a, a second end 69a and a lumen 71a extending therein. Lumen 71a may extend from the first end 67a to the second end 69a. While FIG. 2A depicts the alignment member 64a as a tubular member, other cross-sectional shapes of alignment member 64a are contemplated. For example, the cross-sectional shape of the alignment member 64a may be rectangular, triangular, ovular, square, or the like.

As illustrated, FIG. 2A shows that the alignment member 64a may be disposed along the tether member 62a. For example, in some examples the tether member 62a may extend through the lumen 71a of the alignment member 64a. In at least some examples, the alignment member 64a may permit the tether member 62a to compress into the lumen of the alignment member 64a, such as illustrated in FIG. 3B (with the spaces between the reference markers on the compressed portion of the tether member 62a closer than in FIG. 2A or in FIG. 3A). Therefore, diameter of the lumen of the alignment member 64a needs to be wide enough to permit the tether member 62a to curl upon itself to be "stored" within the lumen of the alignment member 64a. Allowing the tether member 62a to be stored within the lumen of the alignment member 64a may prevent the tether member 62a from being entangled with the first engagement member 52a.

The alignment member 64a illustrated in FIG. 2A is not intended to be limiting. Rather, in some examples, the alignment member 64a may include two mating plastic components that encapsulate one or both of tether members 62a/62b, one or both the engagement members 52a/52b or both the one or more tether members 62a/62b and the one or more engagement members 52a/52b when the tissue retraction device 22 is in the delivery catheter 26 (prior to deployment).

As discussed above, the tissue retraction device 22 may include more than one alignment member (e.g., another alignment member in addition to alignment member 64a described above). For example, the tissue retraction device 22 may include a second alignment member 64b. As shown in FIG. 2A, second alignment member 64b may be a tubular member having a first end 67b, a second end 69b and a lumen 71b extending therein. Lumen 71b may extend from the first end 67b to the second end 69b. While FIG. 2A depicts the alignment member 64b as a tubular member, other cross-sectional shapes of alignment member 64b are contemplated. For example, the cross-sectional shape of the alignment member 64b may be rectangular, triangular, ovular, square, or the like.

As illustrated, FIG. 2A shows that the alignment member 64b may be disposed along the tether member 62b. For example, in some examples the tether member 62b may extend through the lumen 71b of the alignment member 64b. In at least some examples, the alignment member 64b may permit the tether member 62b to compress into the lumen of the alignment member 64b, such as illustrated in FIG. 3B. Therefore, diameter of the lumen of the alignment member 64b needs to be wide enough to permit the tether member 62b to curl upon itself to be "stored" within the lumen of the alignment member 64b. Allowing the tether member 62b to be stored within the lumen of the alignment member 64b may prevent the tether member 62b from being entangled with the second engagement member 52b.

Figure 2B:
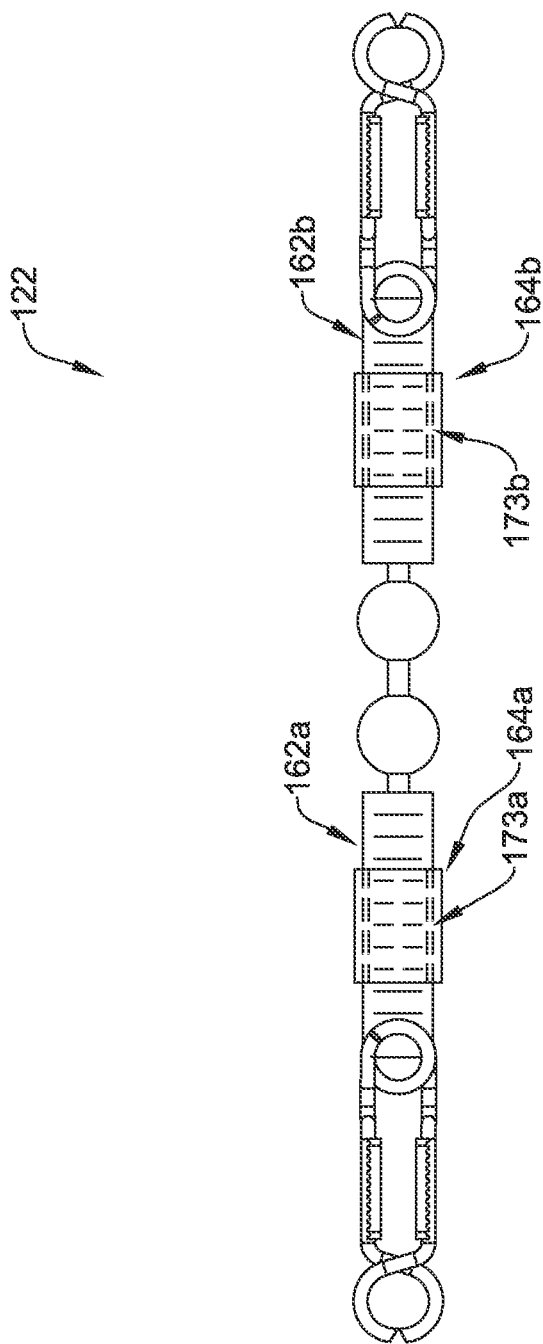
FIG. 2B is a plan view of another example tissue retraction device.

In at least one example tissue retraction device contemplated herein, the tether member may include one or more recessed portions. For example, FIG. 2B illustrates an example tissue retraction device 122 in which the alignment members 164a/164b may mate, fit into, etc. recessed portions 173a/173b (depicted by the dashed lines in FIG. 2B) of the alignment members 164a/164b. It can be appreciated that once the alignment members 164a/164b are disposed along the tether members 162a/162b, they may prevent the tether members 162a/162b from bending and/or folding. In other words, the alignment members 164a/164b may be designed to maintain the tether members 162a/162b in a substantially straight orientation within the delivery catheter 26. It is contemplated that the recessed portions of the alignment members (and corresponding mating portions along the tether members) may be included in any of the tissue retraction devices contemplated herein.

Figure 2C:
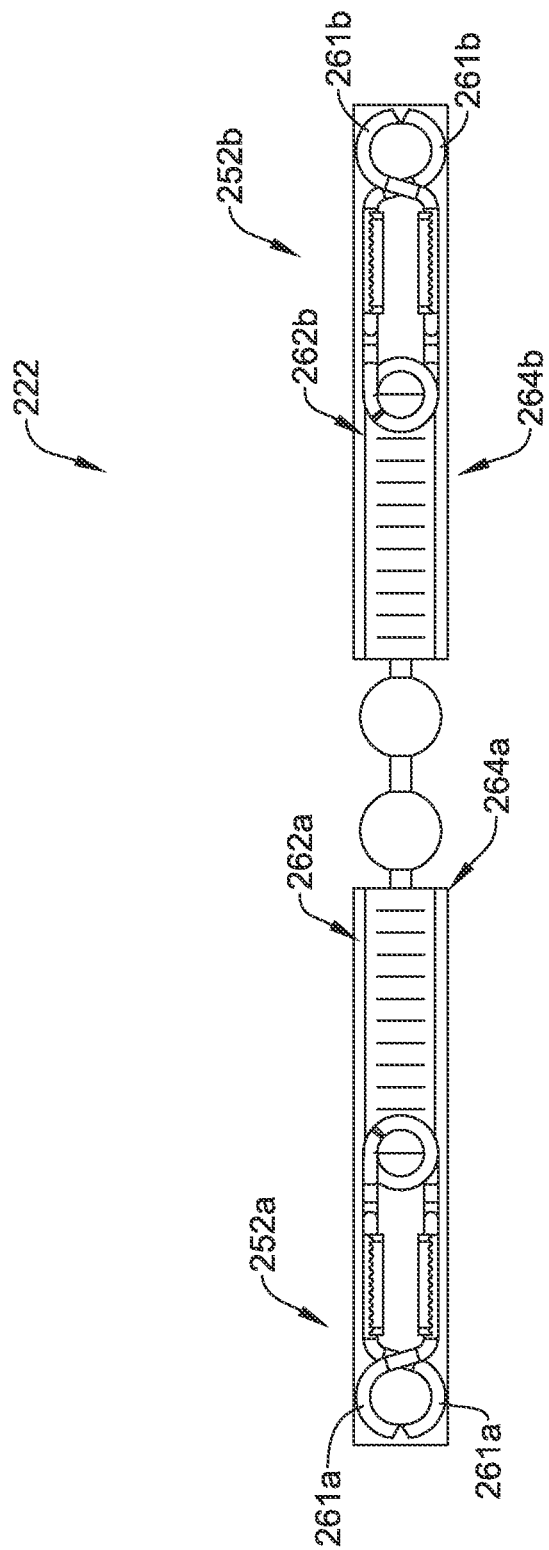
FIG. 2C is a plan view of another example tissue retraction device.

While the above discussion disclosed examples in which the alignment members were disposed along only the tether members, other examples wherein the alignment members extend over both the tether members and the engagement members are contemplated. For example, FIG. 2C illustrates an example tissue retraction device 222 in which the alignment members 264a/264b extend over both the tether members 262a/262b and the engagement members 252a/252b. Allowing the alignment members 264a/264b to extend over both the tether members 262a/262b and the engagement members 252a/252b may assist in the delivery of the tissue retraction device because the alignment members 264a/264b may encapsulate the engagement members 252a/252b, thereby preventing the clip jaws 261a/261b from digging into the delivery catheter (when navigating around a tortuous path, for example). Further, while not shown in the figures, it is contemplated that in some examples a single alignment member may extend over a portion or all of the tissue retraction members described herein.

Additionally, in at least some examples described herein, the alignment members may include sufficient stiffness and column strength to withstand compression during packaging and storage prior to device delivery. Possible materials include polypropylene, PET, thermoplastic elastomers (TPE), polyethylene (PE), or high density polyethylene (HDPE) such as Celanese GUR HOSTALLOY 731.

Figure 2D:
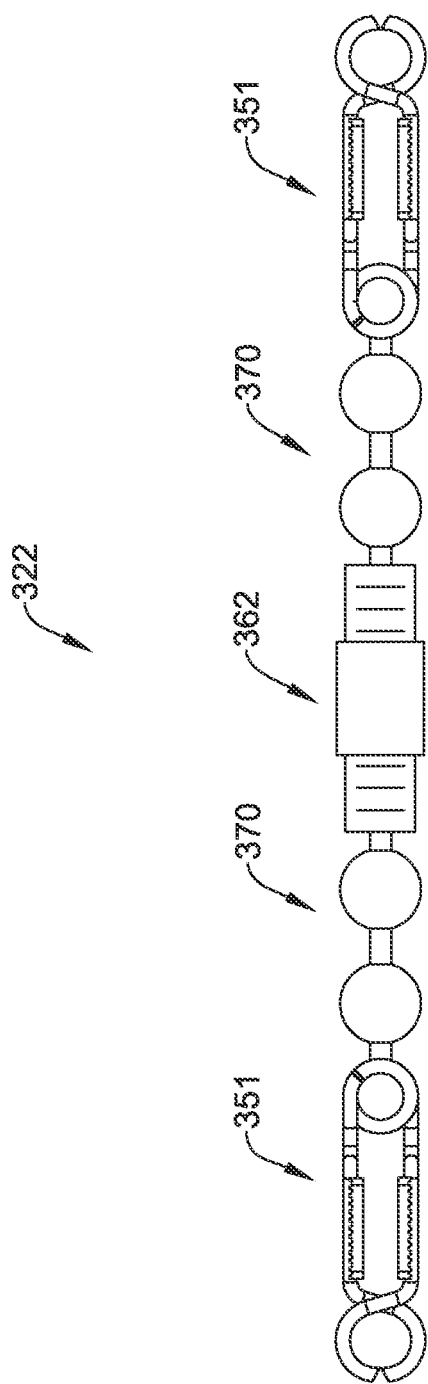
FIG. 2D is a plan view of another example tissue retraction device.

FIG. 2D illustrates another example tissue retraction device 322. As shown in FIG. 2D, the tissue retraction device 322 may include more than one swivel 370. Additionally, each swivel 370 may be directly attached to an engagement member 351. Further, FIG. 2D shows a singular tether member 362 positioned between the swivel members 370. While FIG. 2D shows a single tether member 362 positioned between two swivel members 370, other configurations are contemplated.

Figure 2E:
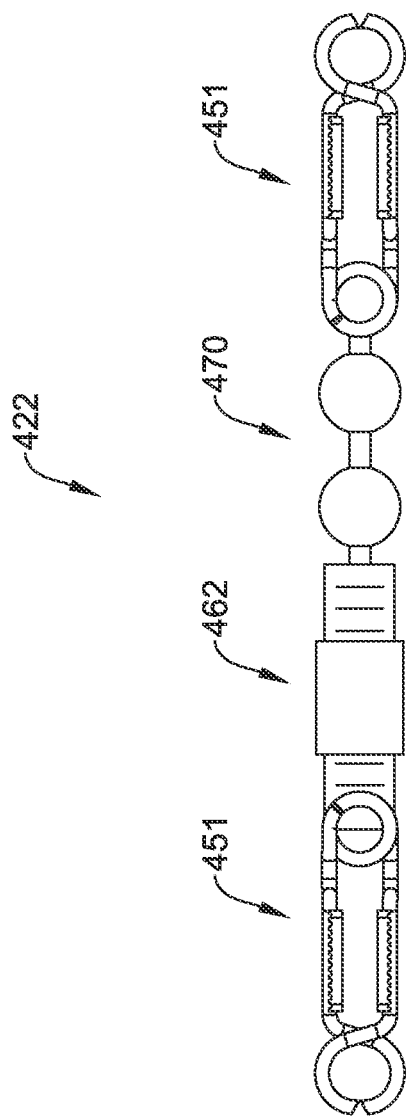
FIG. 2E is a plan view of another example tissue retraction device.

FIG. 2E illustrates another example tissue retraction device 422. As shown in FIG. 2E, the tissue retraction device 422 may include a single tether member 462 directly attached to an engagement member 451 and a swivel member 470 directly attached to an engagement member 451. Further, the tether member 462 and the swivel member 470 may be attached to one another.

FIGS. 2A-2E shows several different embodiments of tissue retraction members having engagement members, tethers, swivels and alignment members arranged in various configurations. It can be appreciated that the configurations shown in FIGS. 2A-2E are not intended to be limiting. Rather, it is contemplated that the number and arrangement/order of the individual components (e.g., engagement members, tethers, swivels and alignment members) utilized in an example tissue retraction device may include configurations other than those disclosed herein.

Figure 4:
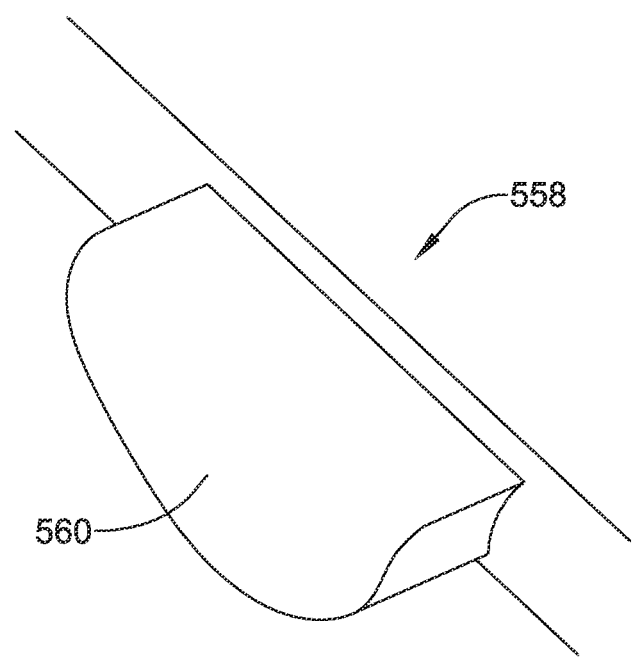
Figure 5:
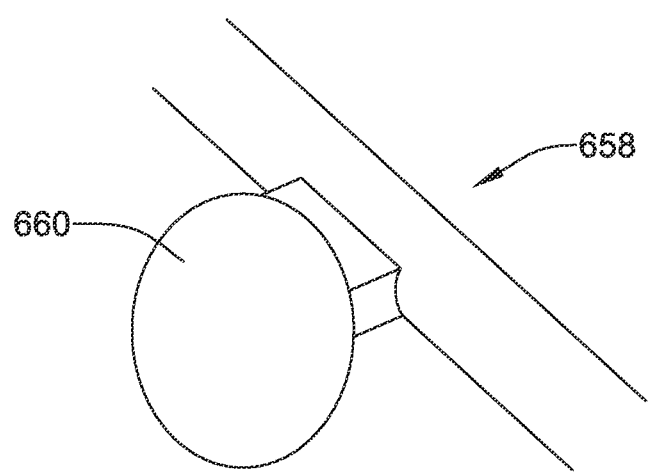
Figure 6:
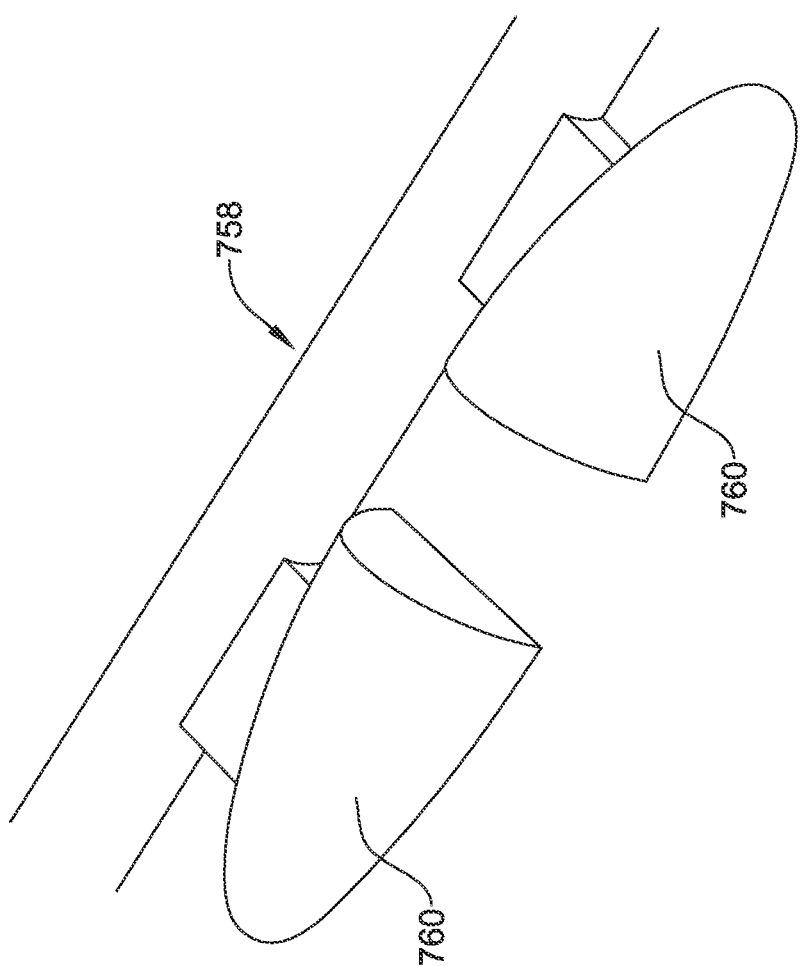
Figure 7:
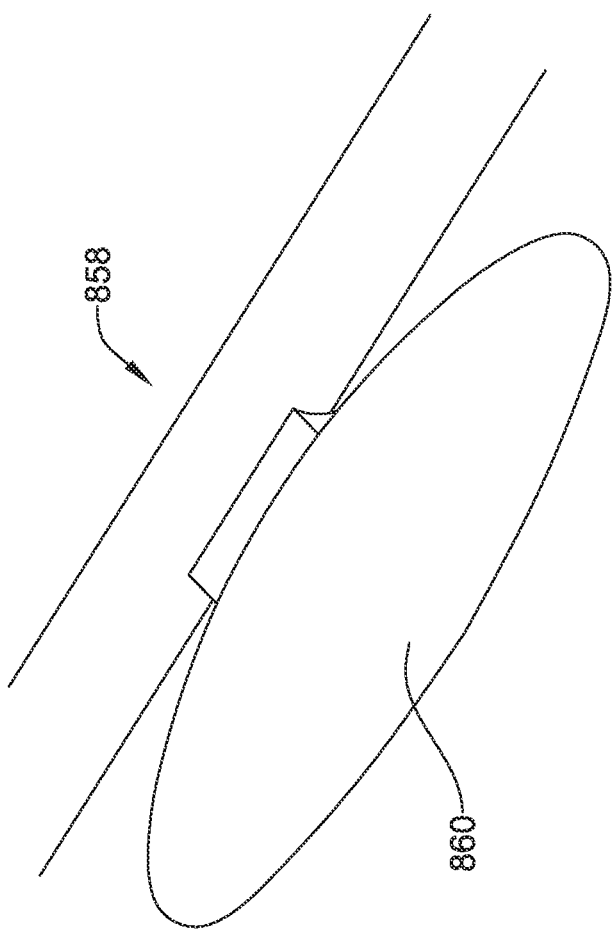
Figure 8:
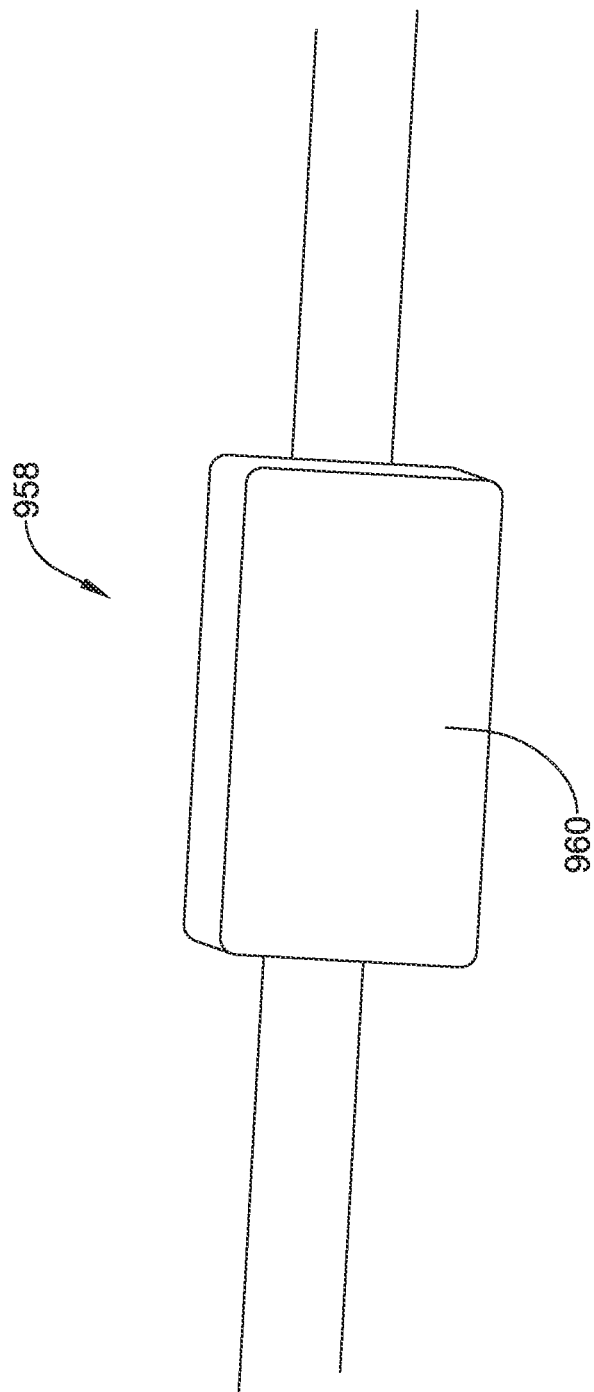

As discussed above, it can be appreciated that a variety of gripping members 58a/58b may be designed to mate with the jaws of the grasping member 39. FIGS. 4-12 illustrate several different gripping member designs that may be utilized with any of the example tissue retraction devices described herein. For example, FIG. 4 illustrates a gripping member 558 that includes a tab and or paddle structure 560. FIG. 5 further illustrates a gripping member 658 that includes a spherical ball 660. FIG. 6 further illustrates a gripping member 758 that includes a bullet or conical shaped member 760. FIG. 7 further illustrates a gripping member 858 that includes an ovular shaped member 860. FIG. 8 further illustrates a gripping member 958 including recessed tabs 960. FIG. 9 further illustrates a gripping member 1058 that includes channels 1060. FIG. 10 further illustrates a gripping member 1158 that includes channels 1160. FIG. 11 further illustrates a gripping member 1258 that includes channels 1260 and recessed portion 1261. FIG. 12 further illustrates a gripping member 1358 including channels 1360. The shapes of the gripping members disclosed above are not intended to be limiting. Rather, the gripping members described herein may also include cups, shells, ribs, hemispheres, tabs, knobs, ovals, pads, or combinations thereof.

As discussed above, the gripping members described herein may be utilized by the manipulator 34 to open and/or close the jaws 61a/61b of the tissue retraction device 22 described herein. For example, FIG. 3A shows the jaws 61a/61b of the tissue retraction device 22 opened to an expanded configuration. As shown in FIG. 3A, the jaws 61a/61b may open to an expanded configuration when the manipulator 34 grasps and squeezes the gripping members 58a/58b together. It can further be appreciated that when the manipulator 34 releases the gripping members 58a/58b, the jaws 61a/61b may close.

FIGS. 13-17 illustrate a series of steps to deploy and utilize the tissue retraction system 10 described above. The tissue retraction device 22 may be utilized to lift and reposition target tissue which has been dissected by a clinician. As will be made clear by the following illustrations, as the clinician cuts away target tissue, the tissue retraction device may lift and reposition it, thereby providing the clinician with an unobstructed view of the ongoing procedure.

Figure 13:
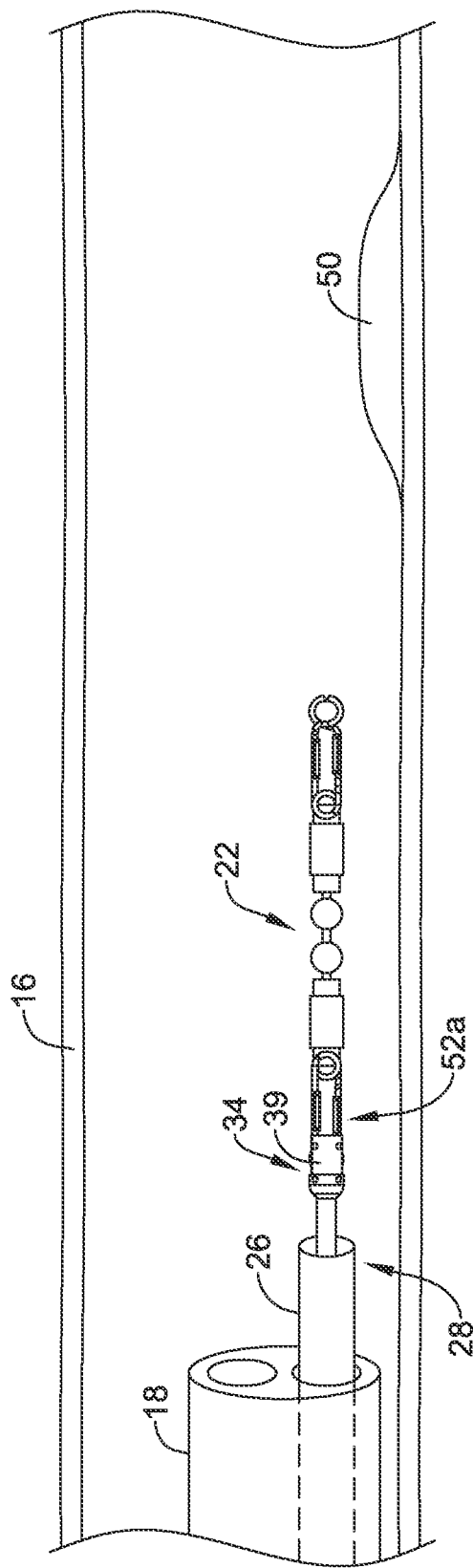
FIGS. 13-17 illustrate a methodology for deploying and attaching an example tissue retraction device.

FIG. 13 illustrates a first step in utilizing the tissue retraction system 10 in a dissection procedure. As described above and illustrated in FIG. 13, the clinician may first advance the manipulator 34 in a proximal-to-distal direction (relative to the distal end 28 of the delivery catheter 26). This forward movement of the manipulator will force the grasping member 39 of the manipulator to push the tissue retraction device 22 forward and out the distal end 28 of the delivery catheter 26. FIG. 13 illustrates the tissue retraction device 22 having been advanced out of the distal end 28 of the delivery catheter 26, whereby it is positioned adjacent to the tissue target 50 (e.g., a cancerous lesion).

Figure 14:
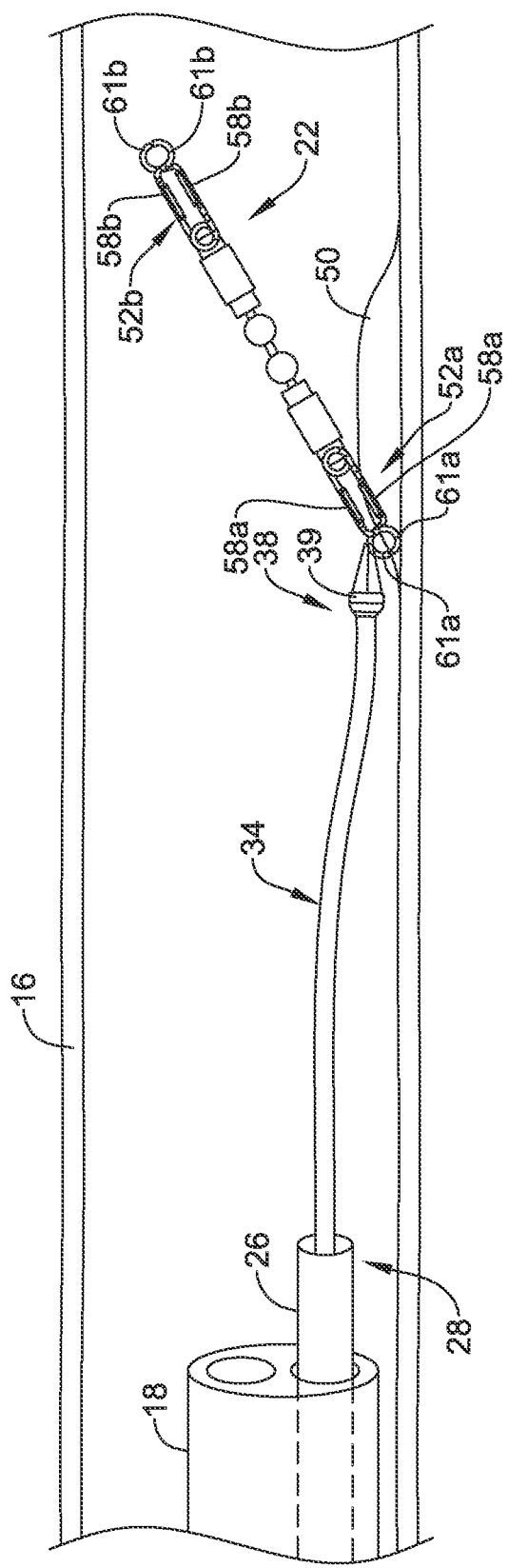

FIG. 14 illustrates an example second step in utilizing the tissue retraction system 10 in a dissection procedure. FIG. 14 illustrates that a clinician may manipulate the distal end 38 of the manipulator 34 to grasp the first engagement member 52a (for clarity, the grasping member 39 is shown in a closed configuration in FIG. 14. It can be appreciated that the grasping member 39 may open up to grasp the first engagement member 52a). For example, the clinician may manipulate the handle 44 of the tissue retraction system 10 to open the jaws of the grasping member 39. Once opened, the jaws of the grasping member may engage the gripping members 58a of the first engagement member 52a. After engaging the gripping members 58a, the clinician may close the jaws of the grasping member 39, thereby opening the jaws 61a of the first engagement member 52a. Using the grasping member 39, the clinician may then position the jaws 61a onto the surface of the target tissue 50. By releasing the grasper 39 from the gripping members 58b, the jaws 61a of the first engagement member 52a may close and attach the jaws 61a (and, by extension, the first engagement member 52a) to the surface of target tissue 50.

Figure 15:
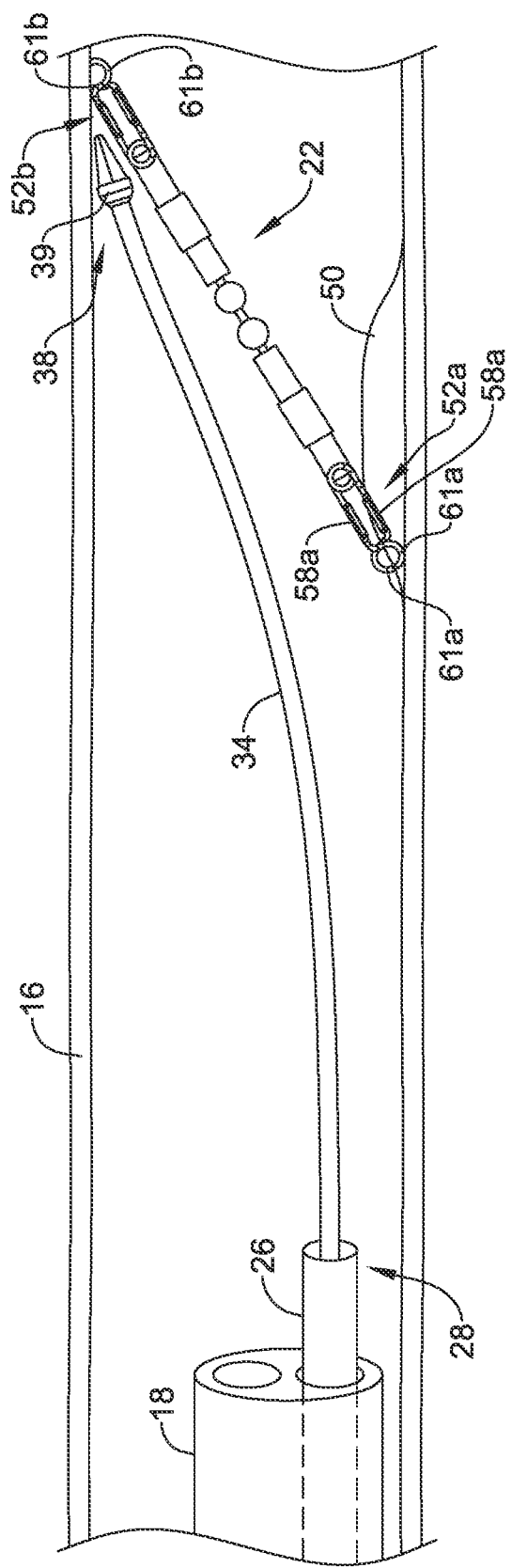

FIG. 15 illustrates an example third step in utilizing the tissue retraction system 10 in a dissection procedure. FIG. 15 illustrates that a clinician may manipulate the distal end 38 of the manipulator 34 to grasp the second engagement member 52b (for clarity, the grasper 39 is shown in a closed configuration in FIG. 15. It can be appreciated that the grasper 39 may open up to grasp the second engagement member 52b). For example, the clinician may manipulate the handle 44 (described above) of the tissue retraction system 10 to open the jaws of the grasper 39. Once opened, the jaws of the grasper may engage the gripping members 58b of the second engagement member 52b. After engaging the gripping members 58b, the clinician may close the jaws of the grasper 39, thereby opening the jaws 61b of the second engagement member 52b. The clinician may then pull on the second engagement member 52b, thereby lengthening the tissue retraction device 22 (as described above with respect to FIG. 2A and FIG. 3A). Once the tissue retraction device is elongated to a desired length (which may be confirmed visually via reference markers 66 as described above), the clinician may position the jaws 61b of the second engagement member 52b onto the surface of the target tissue site 50. By releasing the grasping member 39 from the gripping members 58b, the jaws 61b of the second engagement member 52b may close, thereby attaching the jaws 61b (and, by extension, the second engagement member 52b) to the inner surface of body lumen 16.

Figure 16:
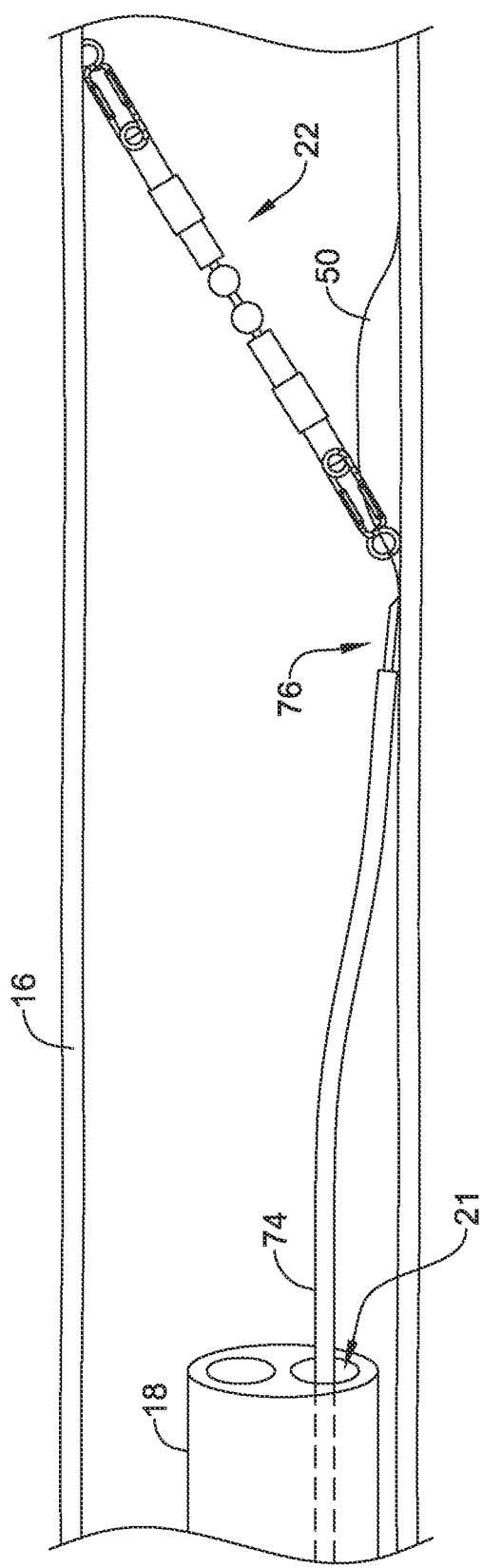

FIG. 16 illustrates an example fourth step in utilizing the tissue retraction system 10 in a dissection procedure. FIG. 16 illustrates that after the tissue retraction device 22 has been attached to both the target tissue site 50 and to the inner surface of the body lumen 16 at a position spaced away from the target tissue site (which places the tissue retraction device 22 in tension), the clinician may exchange the manipulator 34 for a cutting tool 74. The cutting tool 74 may include a cutting member 76 positioned at the target tissue 50. Further, the cutting tool 74 may be advanced within the working channel 21 of the medical device 18 as described above.

Figure 17:
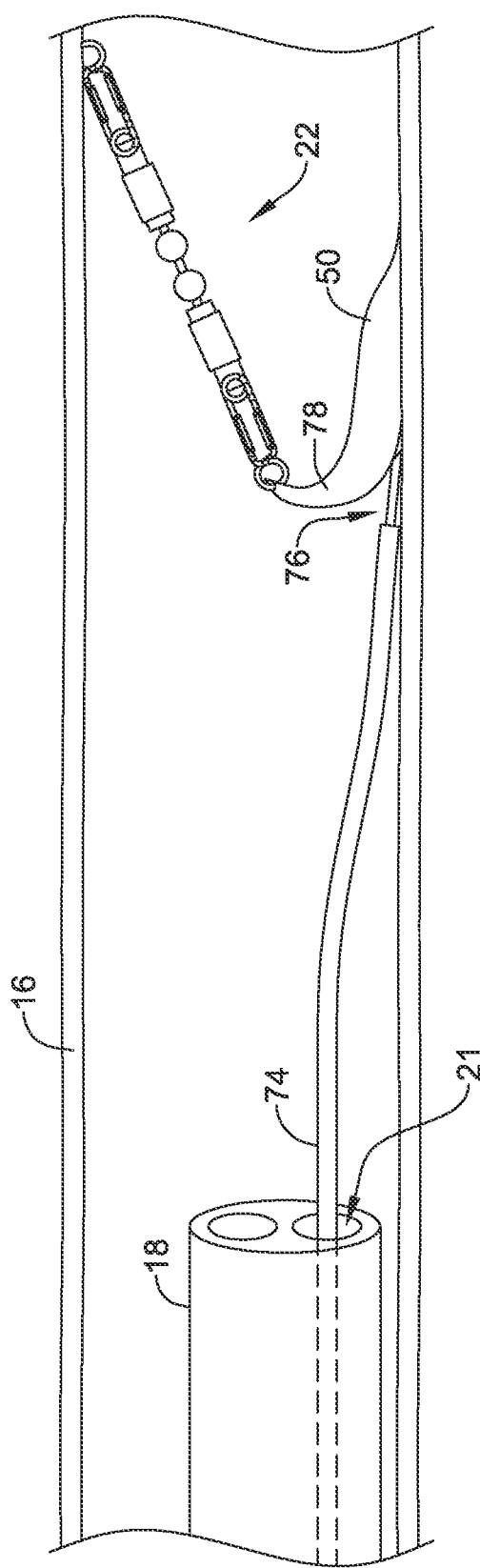

FIG. 17 illustrates an example fifth step in utilizing the tissue retraction system 10 in a dissection procedure. FIG. 17 illustrates the clinician performing the tissue dissection by utilizing the cutting tool 74 to cut a portion of the target tissue 50. As can be appreciated from FIG. 17, as the cutting tool 74 cuts a portion of the target tissue 50, the tissue retraction device 22 retracts (via the retraction of tether members 62a/62b), and thereby lifts the dissected portion 78 of the target tissue 50 up and away from the plane of tissue being cut by the physician. By lifting and retracting the dissected portion 78 of the target tissue 50, a clear, unobstructed view of the procedure is maintained for the clinician. It is noted that, if necessary, the engagement members 52a/52b of the tissue retraction system 10 may be repositioned. In other words, adjustments in tension and/or direction may be imparted into the tissue retraction system 10 as desired.

In some instances, after having been deployed from the distal end 28 of the delivery catheter 26 (e.g., illustrated and described with respect to FIG. 13), the tissue retraction device 22 may come to rest in a flat configuration along the inner surface of the body lumen 16. It can be appreciated that it may be difficult for a clinician to utilize the manipulator 34 to grasp the first engagement member 52a and/or second engagement member 52b when the tissue retraction device 22 is lying in a flat configuration. Therefore, in some examples described herein the tissue retraction device 22 may include a component designed to space the first engagement member 52a and/or the second engagement member 52b away from the inner surface of the body lumen 16 such that the engagement members 52a/52b are in a position/ configuration which allows easier grasping/manipulation thereof.

Figure 18:
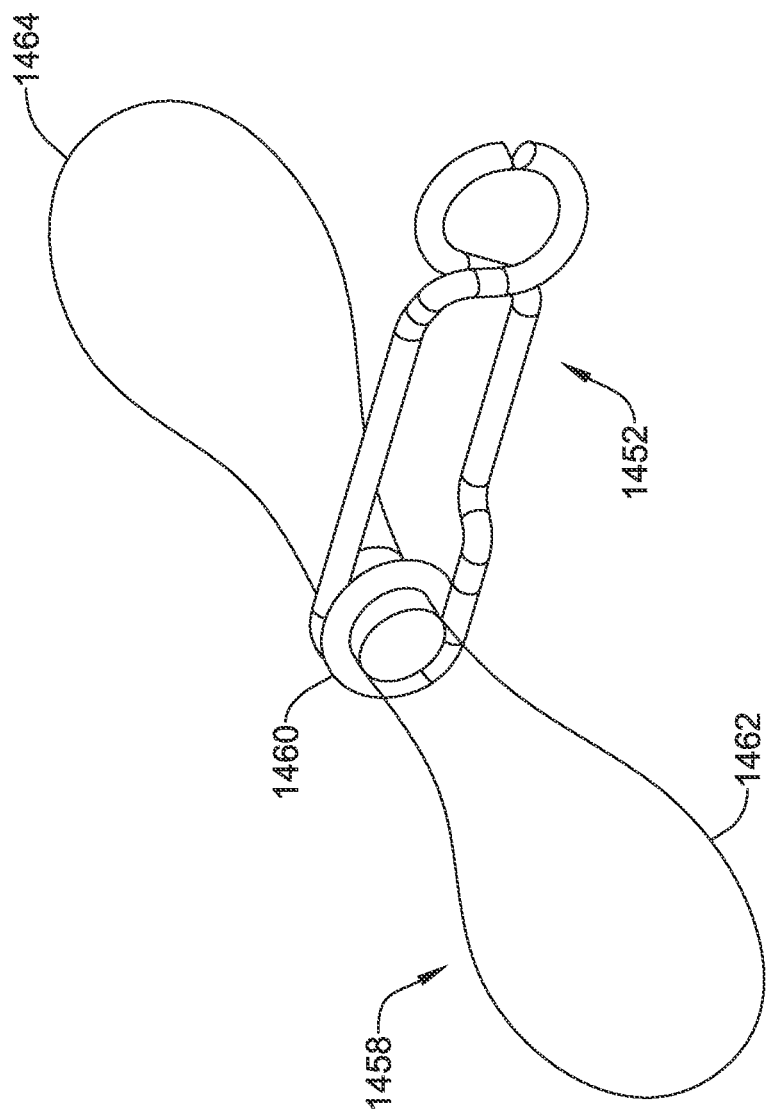
FIG. 18 illustrates a perspective view of a portion of another example tissue retraction device.

For example, FIG. 18 shows an example engagement member 1452 including a wing member 1458. Wing member 1458 may include a first wing 1462 and a second wing 1464. The first wing 1462 may be on the opposite side of the engagement member 1452 relative to the second wing 1464. In some examples, the first wing 1462 may be symmetrical to the second wing 1464. However, in other examples, the first wing 1462 may include a design geometry which is different from the second wing 1464. Further, the first wing 1462 and the second wing 1464 may include any number of curves, contours, bends, etc. which are designed to keep the engagement member in a substantially upright configuration. In other words, the first wing and/or the second wing 1464 may be designed to maintain the engagement member 1452 in substantially upright configuration (e.g., in a configuration that whereby the engagement member is not lying flat along an inner surface of the body lumen 16). While FIG. 18 shows the wing 1458 extending through the spring 1460 of engagement member, this is not intended to be limiting. Rather, it is contemplated that the wing 1458 may be positioned and/or disposed along any portion of the engagement member 1452.

Figure 19:
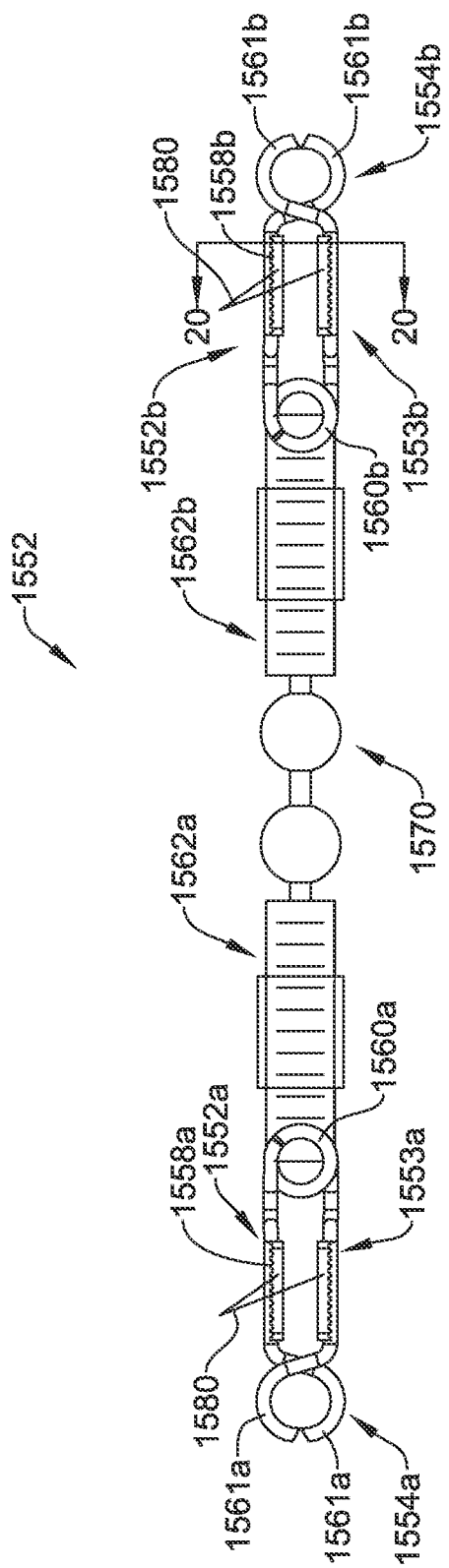
FIG. 19 is a plan view of another example tissue retraction device.

FIG. 19 illustrates another example tissue retraction device 1522. Similar to the examples described above, FIG. 19 illustrates that the tissue retraction device 1522 may include a first engagement member 1552a and a second engagement member 1552b. The first engagement member 1552a may include a tissue engagement portion 1554a and an actuation portion 1553a. The tissue engagement portion 1554a may include a one or more jaws 1561a. The jaws 1561a may be designed such that they move relative to one another. FIG. 19 further illustrates that the first engagement member 1552a may include a spring element 1560a. It can be appreciated that the spring element 1560a may be designed to provide a compressive force that is translated through the actuation portion of the first engagement member 1552a to the jaw members 1561a, thereby biasing the jaw members 1561a in a closed position (e.g., a position in which the jaw members 1561a are contacting one another). However, the ends of the jaw members 1561a may not necessarily contact one another while in a closed position. The jaw members 1561a may be spaced apart from one another while in a closed position. Additionally, similarly to that described above, FIG. 19 further illustrates that the first engagement member 1552a may include one or more gripping members 1558a positioned along the actuation portion 1553a. It can be appreciated that the engagement member first 1552a depicted in the examples disclosed herein is schematic. In other words, it is contemplated that the engagement member 1552a described herein may include alternative design arrangements, features, geometries etc. without departing from the scope of the examples contemplated herein.

As discussed above, the tissue retraction device 1522 may include more than one engagement member (e.g., another engagement member in addition to the first engagement member 1552a described above). For example, FIG. 19 illustrates that the tissue retraction device 1522 may include a second engagement member 1552b. The second engagement member 1552b may include a tissue engagement portion 1554b and an actuation portion 1553b. The tissue engagement portion 1554b may include a one or more jaws 1561b. The jaws 1561b may be designed such that they move relative to one another. FIG. 19 further illustrates that the second engagement member 1552b may include a spring element 1560b. It can be appreciated that the spring element 1560b may be designed to provide a compressive force that is translated through the actuation portion of the second engagement member 1552b to the jaw members 1561b, thereby biasing the jaw members 1561b in a closed position (e.g., a position in which the jaw members 1561b are contacting one another). However, the ends of the jaw members 1561b may not necessarily contact one another while in a closed position. The jaw members 1561b may be spaced apart from one another while in a closed position. Additionally, similarly to that described above, FIG. 19 further illustrates that the second engagement member 1552b may include one or more gripping members 1558b positioned along the actuation portion 1553b. It can be appreciated that the second engagement member 1552b depicted in the examples disclosed herein is schematic. In other words, it is contemplated that the second engagement member 1552b described herein may include alternative design arrangements, features, geometries etc. without departing from the scope of the examples contemplated herein.

FIG. 19 further illustrates that the tissue retraction device 1522 may include one or more tether members 1562a and 1562b coupled to the first engagement member 1552a, the second engagement member 1552b or both the first engagement member 1552a and the second engagement member 1552b. The tethers 1562a/1562b may be referred to as a band, rope, cord, leash, strap, strand, etc. The tether 1562 may include a variety of cross-sectional geometries. For example, the tether may be circular, rectangular, triangular, or the like. Further, the tethers 1562a/1562b may be bioabsorbable.

FIG. 19 further illustrates that in some examples, the tissue retraction device 1522 may include a swivel 1570. As shown in FIG. 19, first engagement member 1552a and first tether 1562a to rotate independently around a central axis of the tissue retraction device 1522 relative to the second engagement member 1552b and the second tether 1562b. The swivel 1570 may be designed to provide complete rotation (e.g., 360 degree rotation) of the first engagement member 1552a and first tether 1562a relative to the second engagement member 1552b and the second tether 1562b. However, in other examples, swivel 1570 may be designed provide only partial rotation (e.g., less than 360 degree rotation) of the first engagement member 1552a and first tether 1562a relative to the second engagement member 1552b and the second tether 1562b. It can be appreciated that the swivel 1570 depicted in the examples disclosed herein is schematic. In other words, it is contemplated that the swivel 1570 described herein may include alternative design arrangements, features, geometries etc. without departing from the scope of the examples contemplated herein.

FIG. 19 further illustrates that the first engagement member 1552a and/or the second engagement member 1552b may include one or more interface members 1580. The interface members 1580 may include a strap, wire, string, loop, etc. having a first end and a second end which are coupled to a portion of the engagement members 1552a and 1552b. The interface members 1580 may be attached to a portion of the actuation portion 1553a/1553b. However, while FIG. 19 shows the interface members 1580 coupled to the actuation portion 1553a/1553b, it is also contemplated that in some examples, the interface members 1580 may be coupled to other portions of the engagement members 1552a/1552b. For example, the interface members 1580 may be coupled to the gripping members 1558a/1558b.

As illustrated in FIG. 19, the interface members 1580 may extend away from the engagement members 1552a and/or 1552b. For example, the interface member 1580 illustrated in FIG. 19 may be conceptualized as extending out of the page, and therefore, forms a configuration which resembles an arch or a loop with respect to the engagement members 1552a/1552b.

Figure 20:
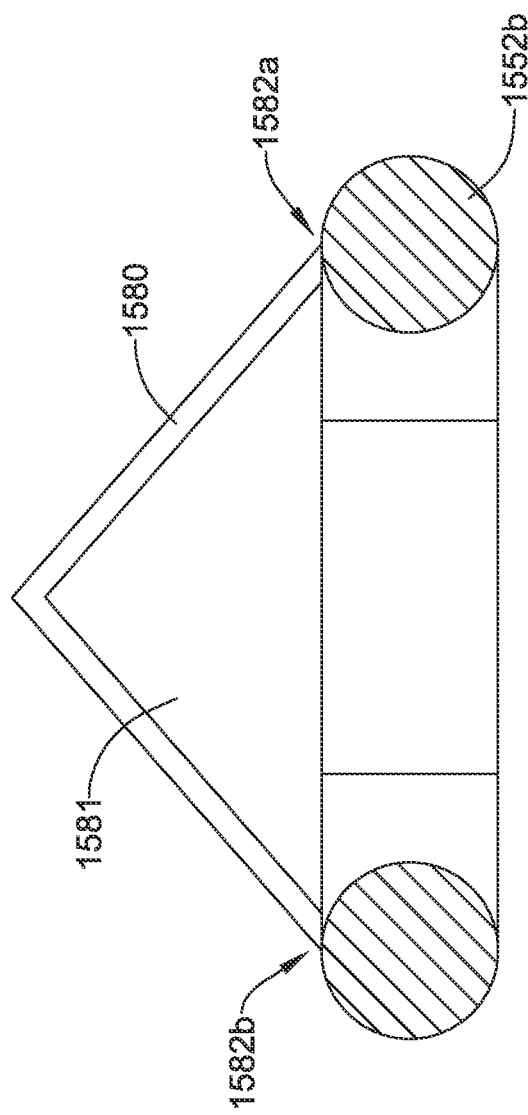
FIG. 20 is a partial cross-sectional view of the tissue retraction device taken along line 20-20 of FIG. 19.

FIG. 20 is a cross-sectional view taken along line 20-20 of FIG. 19. FIG. 20 illustrates the interface member 1580 extending away from the engagement member 1552b. As shown in FIG. 20, interface member 1580 may be coupled to the engagement member 1552b at a first connection point 1582a and a second connection point 1583b. Additionally, as described above, the interface member may be formed into an arch or loop which creates an open space 1581. Further, while FIG. 20 illustrates the interface member 1580 coupled to the engagement member 1552b, it is contemplated that the interface member 1580 coupled to the engagement member 1552a may configured similar to that described with respect to engagement member 1552b illustrated in FIG. 20.

Figure 21A:
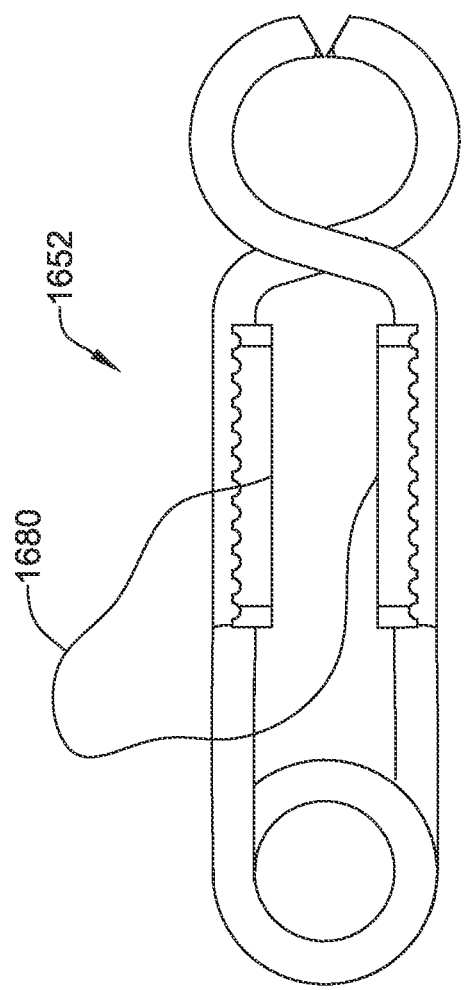
FIG. 21A is a plan view of a portion of an example tissue retraction device.

FIG. 21A illustrates an example engagement member 1652 including an example interface member 1680. The interface member 1680 shown in FIG. 21A may include a strap, wire, loop, or the like.

Figure 21B:
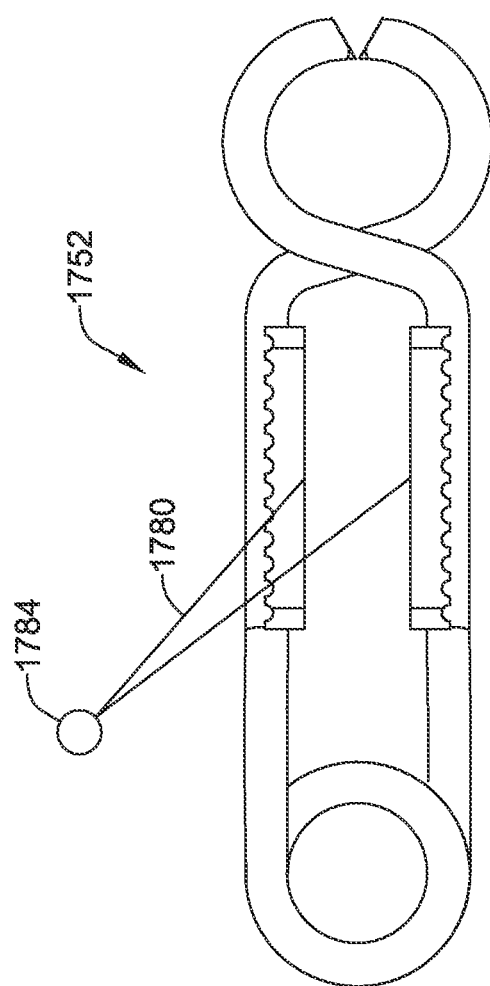
FIG. 21B is a plan view of a portion of an example tissue retraction device.

FIG. 21B illustrates an example engagement member 1752 including an example interface member 1780. The interface member 1780 shown in FIG. 21A may include a wire or rigid member. Additionally, the interface member 1780 may include a ring portion 1784.

Figure 21C:
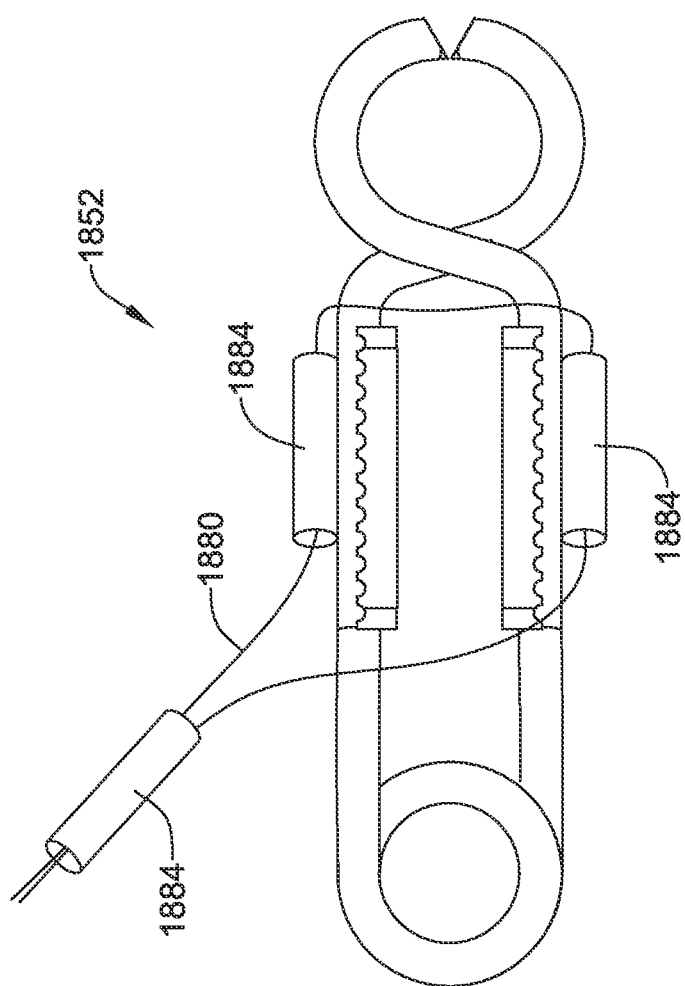
FIG. 21C is a plan view of a portion of an example tissue retraction device.

FIG. 21C illustrates an example engagement member 1852 including an example interface member 1880. The interface member 1880 shown in FIG. 21A may include a strap, wire, loop, or the like. Additionally, the interface member 1880 may include one or more tubular members 1884 which may be attached to a portion of the engagement member 1852. Additionally, as illustrated in FIG. 21C, the interface member may extend within or through one or more of the tubular members 1884.

Figure 22:
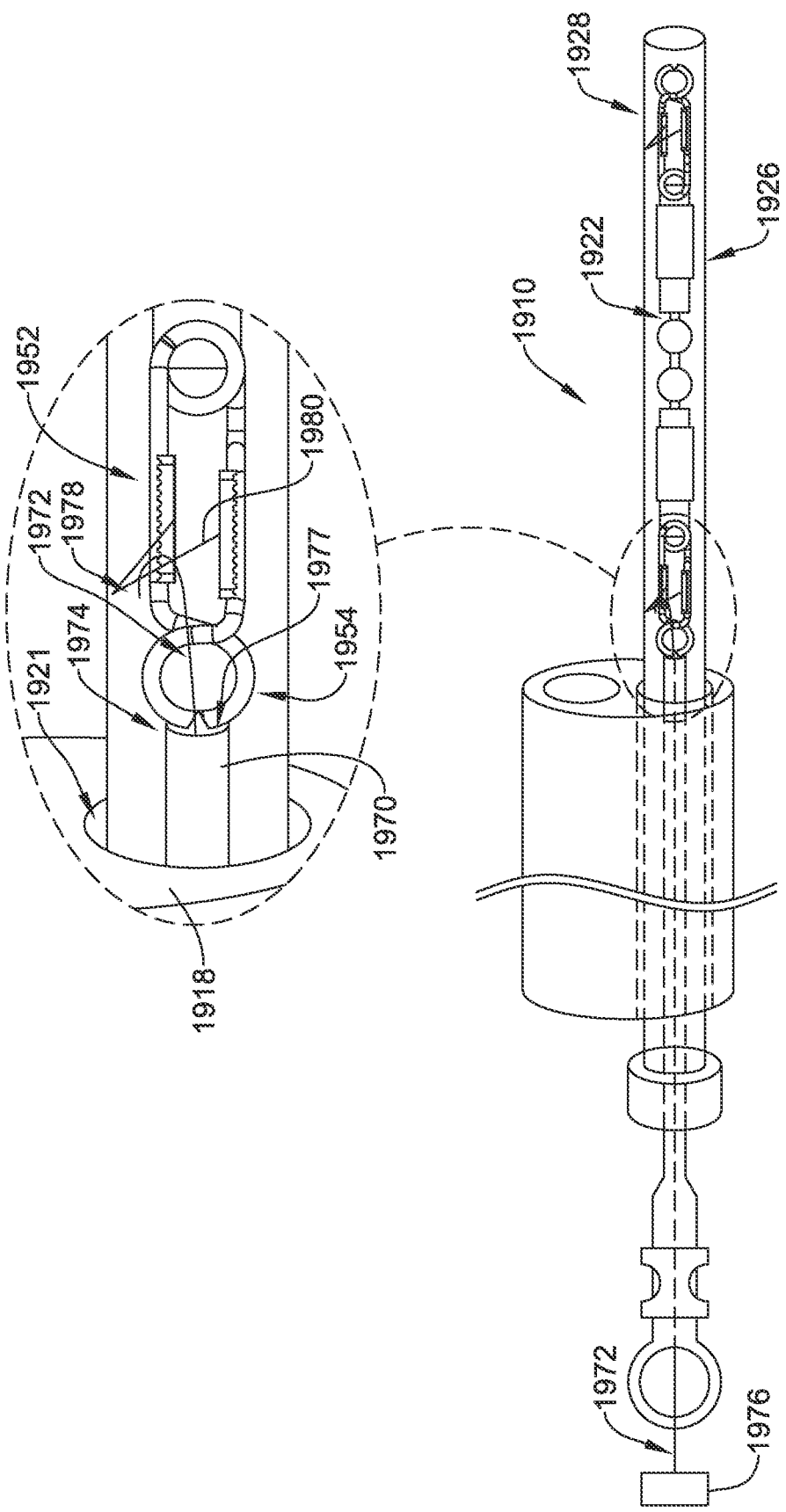
FIG. 22 illustrates an example tissue retraction device positioned in a delivery catheter.

FIG. 22 illustrates an example tissue retraction delivery system 1910. The tissue retraction delivery system 1910 includes a tissue retraction device 1922 positioned within a delivery catheter 1926. Tissue retraction device 1922 and delivery sheath 1926 may be similar in form and function to other examples disclosed above. Further, the detailed view of FIG. 22 further illustrates that, in some examples, the tissue retraction delivery system 1910 may include a support catheter 1970. The support catheter 1970 may extend within a lumen 1921 of a medical device 1918. However, this is not intended to be limiting. Rather, in some examples a support catheter may not be present in the tissue retraction delivery system 1910.

In some examples, a distal end 1974 of the support catheter 1970 may be positioned adjacent a tissue engagement region 1954 of a tissue engagement member 1952. It can be appreciated that the distal end 1974 of the support catheter 1970 may be designed such that it does not permit the tissue engagement member 1952 from entering a lumen 1977 thereof. For example, the diameter of lumen 1977 of the support catheter 1970 may be sized such that the tissue engagement region 1954 of the tissue engagement member 1952 may be prevented from entering therein. Consequently, it can be appreciated that advancing the support catheter 1970 in a proximal-to-distal direction may "push" the tissue retraction device 1922 distally within the delivery sheath 1926. This mechanism of deploying the tissue retraction device 1922 out of the delivery sheath 1926 via proximal-to-distal advancement of the support catheter 1970 will be discussed in greater detail below.

FIG. 22 further illustrates that in at least one example contemplated herein, the tissue delivery system 1910 may include a pull-back member 1972 extending with the lumen 1977 of the support catheter 1970. The pull-back member 1972 may include an attachment portion 1978 positioned on a distal end thereof. Further, as shown in the detailed view of FIG. 22, the attachment portion 1978 of the pull-back member 1972 may engage with an interface member 1980 coupled to the tissue retraction device 1922. For example, the pull-back member 1972 shown in FIG. 22 may include a "hook" which engages (e.g., directly contacts) the interface member 1980. The pull-back member 1972 may be engaged with the interface member 1980 while positioned within the delivery sheath 1926.

Additionally, in some examples, the pull-back member 1972 may not be engaged with the interface member 1980 while positioned within the delivery sheath. Rather, in some examples the distal end of the pull-back member 1972 may be positioned adjacent the proximal end of the tissue engagement region 1954 of the tissue engagement member 1952. Consequently, in these examples, it can be appreciated that advancing the pull-back member 1972 in a proximal-to-distal direction may "push" the tissue retraction device 1922 distally within the delivery sheath 1926.

It is contemplated that the support member 1970 and the pull-back member 1972 may be able to translate with respect to one another. For example, FIG. 22 illustrates that the pull-back member 1972 may extend through the lumen 1977 of the support catheter 1970 to a position in which it is located outside of the body. The proximal end of the pull-back member 1972 may include a handle member 1976. The handle 1976 may be utilized to move the pull-back member 1972 within the lumen 1077 of the support catheter 1970.

Figure 23A:
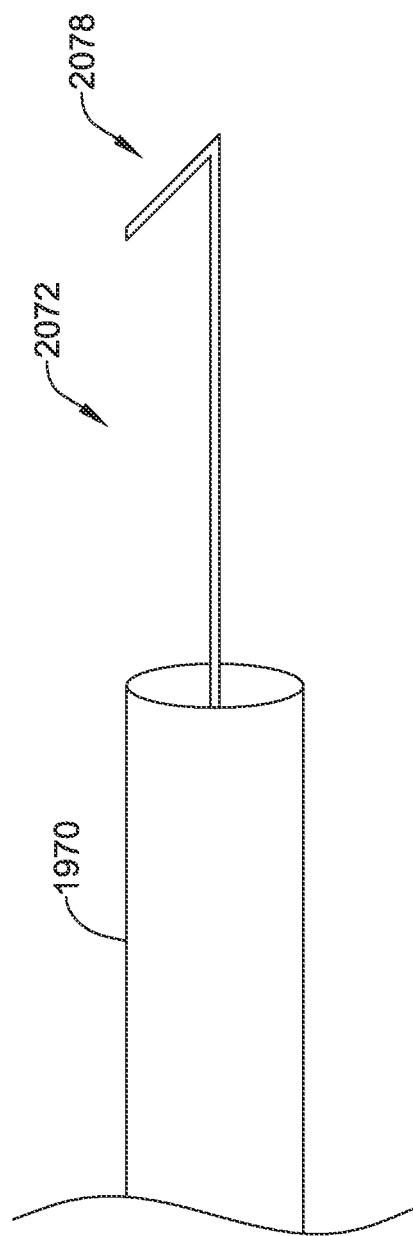
FIGS. 23A-23J illustrate example pull-back members.
Figure 23B:
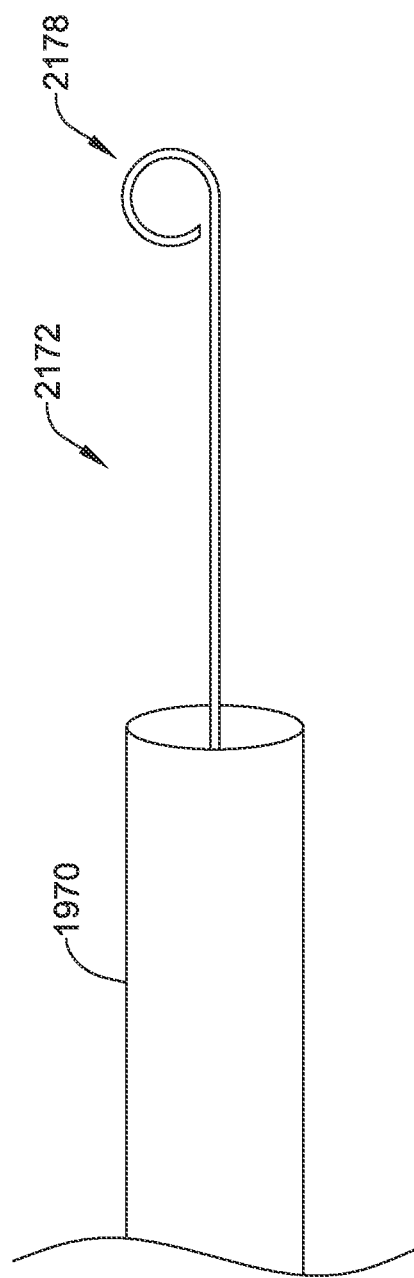
Figure 23C:
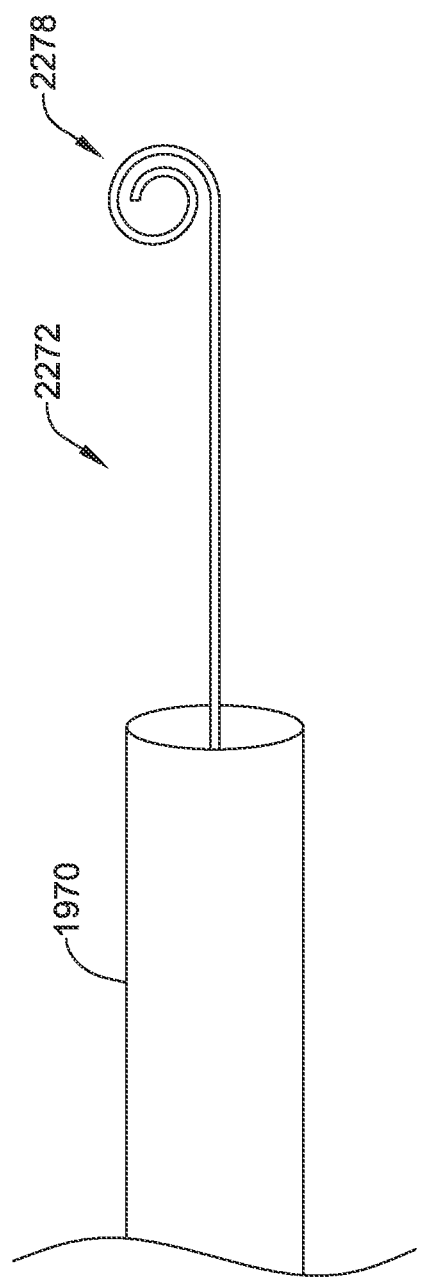
Figure 23D:
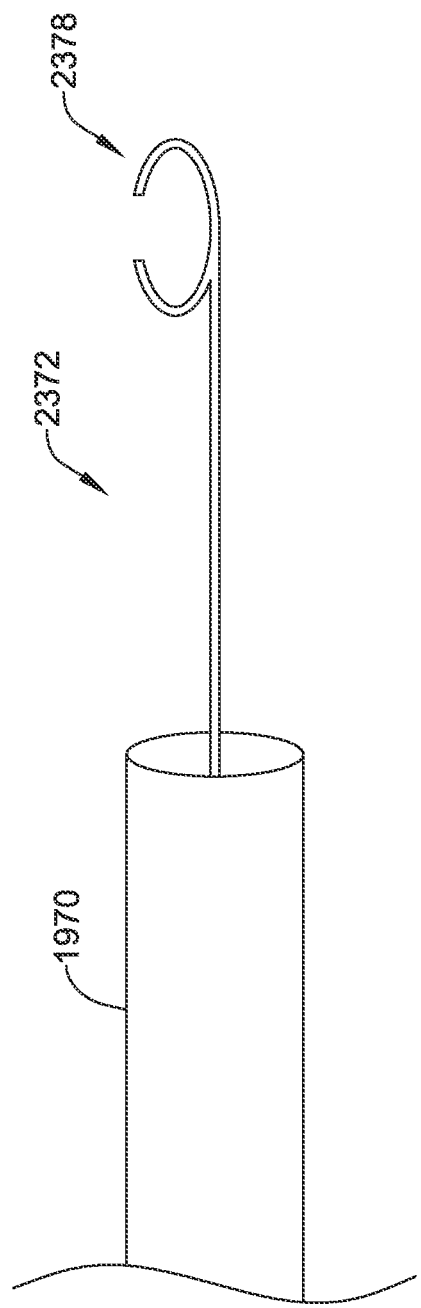
Figure 23E:
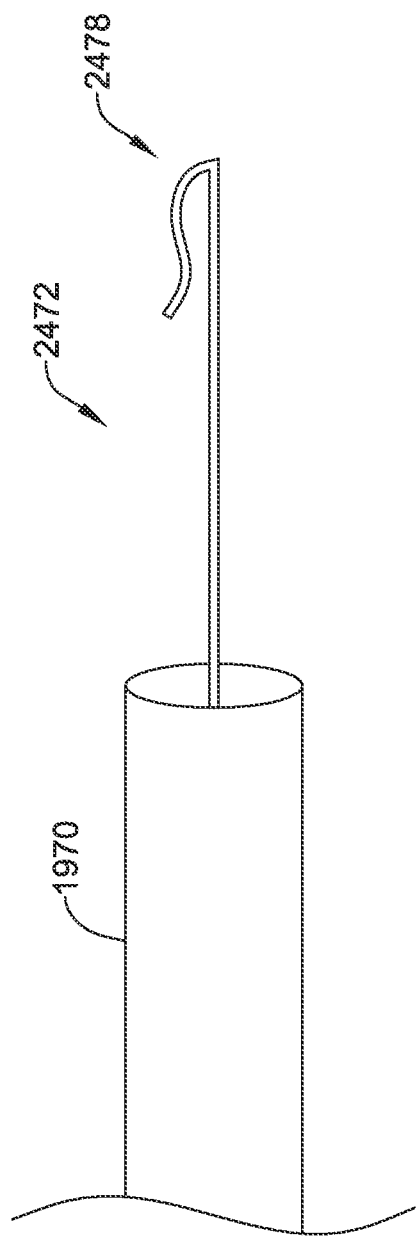
Figure 23F:
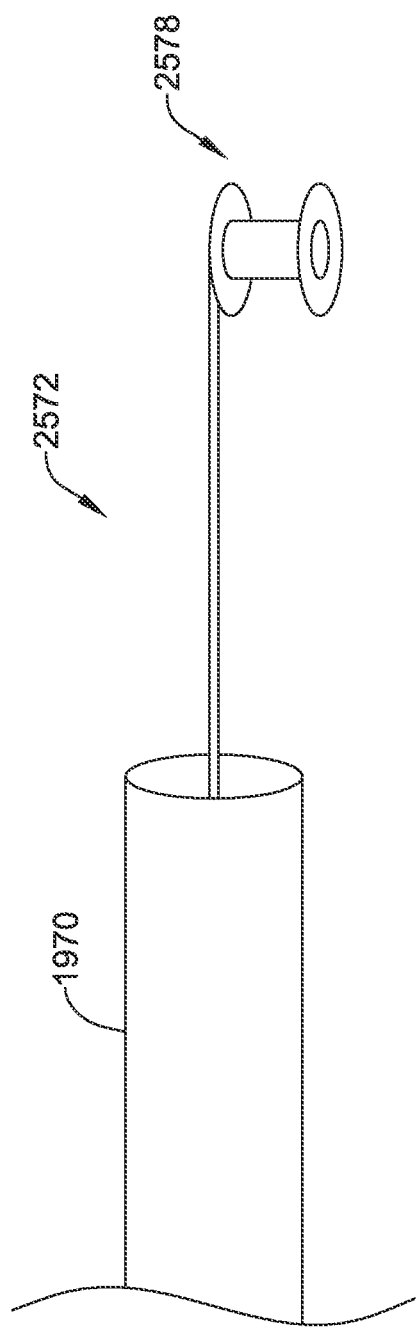
Figure 23G:
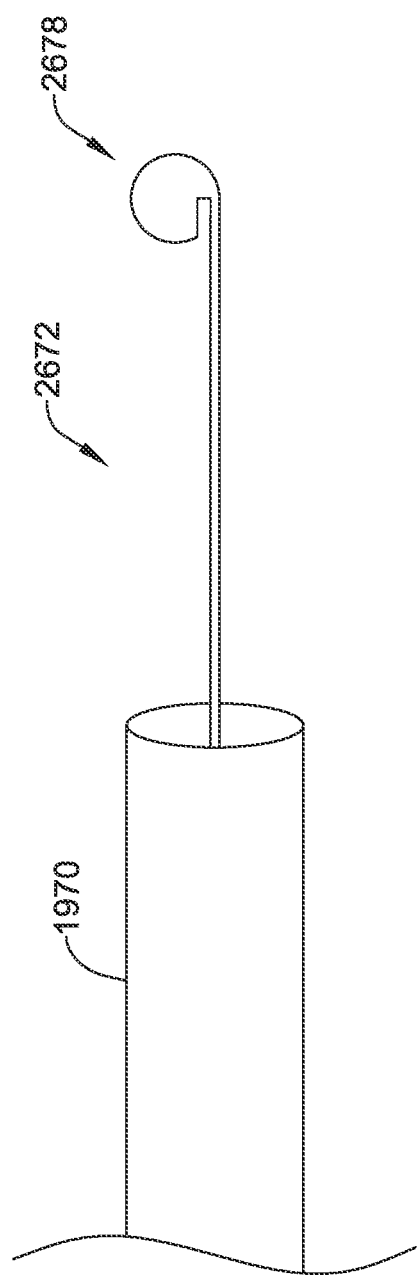
Figure 23H:
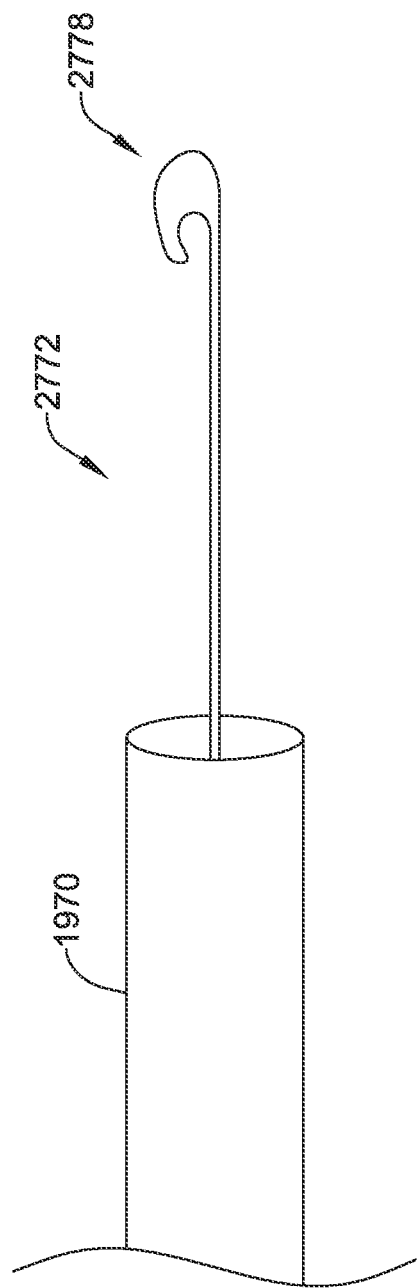
Figure 23I:
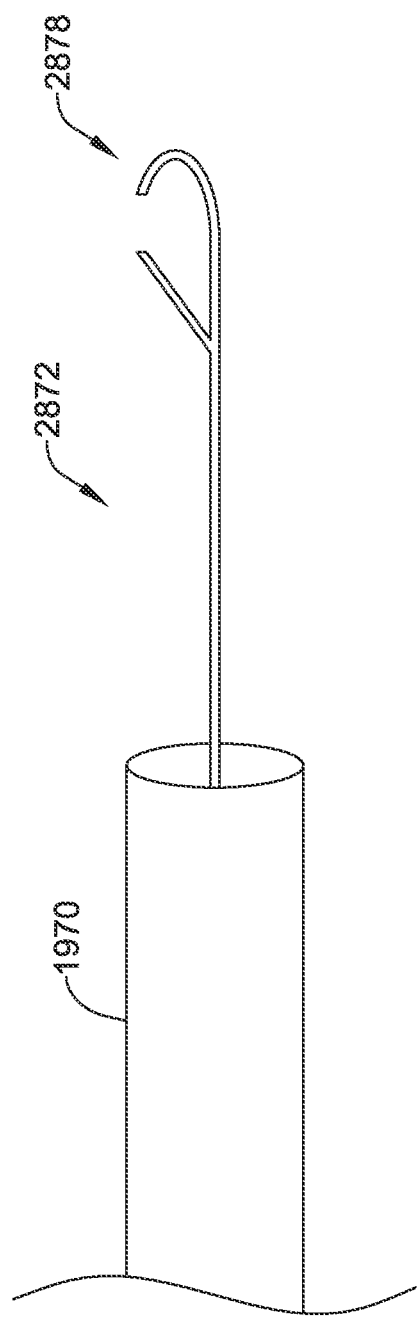
Figure 23J:
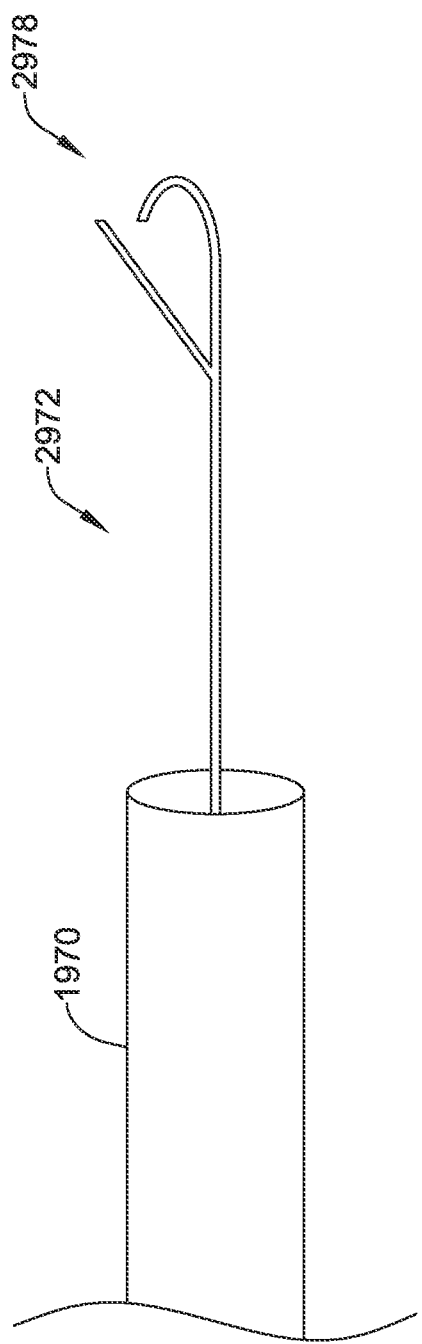

It can be appreciated that the distal end of the pull-back member 1972 may include a variety of design configurations. For example, FIGS. 23A-23J illustrate several different designs that may be utilized with any of the example pull-back members described herein. Further, each of the examples described in FIGS. 23A-23J may be designed to be utilized with support catheter 1970. FIG. 23A illustrates a pull-back member 2072 that includes a hook configuration 2078. FIG. 23B illustrates a pull-back member 2172 that includes a partial loop member 2178. FIG. 23C illustrates a pull-back member 2272 that includes a spiral member 2278. FIG. 23D illustrates a pull-back member 2372 that includes a partial-oval member 2378. FIG. 23E illustrates a pull-back member 2472 that includes a shepard's hook 2478. FIG. 23F illustrates a pull-back member 2572 that includes a spool member 2578. FIG. 23G illustrates a pull-back member 2672 that includes a geometric hoop member 2678. FIG. 23H illustrates a pull-back member 2772 that includes a geometric hoop member 2778. FIG. 23I illustrates a pull-back member 2872 that includes a geometric hoop member 2878. FIG. 23J illustrates a pull-back member 2972 that includes a geometric hoop member 2978. The shapes of the distal end of the pull-back members disclosed above are not intended to be limiting. Rather, the pull-back members described herein may also include a snare, ball, roller, loop, tabs, ovals, triangles, squares, circles, projections, spikes, or combinations thereof.

FIGS. 24-29 illustrate a series of example steps to deploy and utilize the tissue retraction system 1910 described above. Similarly to that described above with respect to tissue retraction device 22, the tissue retraction device 1922 may be utilized to lift and reposition target tissue which has been dissected by a clinician. As will be made clear by the following illustrations, as the clinician cuts away target tissue, the tissue retraction device may lift and reposition the dissected tissue, thereby providing the clinician with an unobstructed view of the ongoing procedure.

Figure 24:
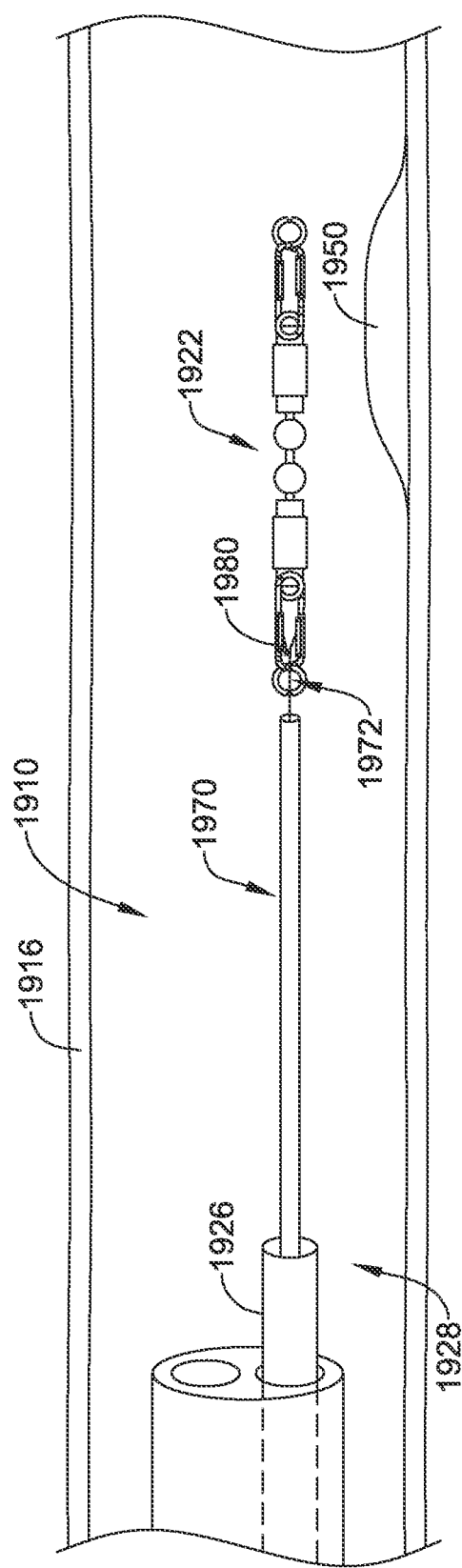
FIGS. 24-29 illustrate a methodology for deploying and attaching an example tissue retraction device.

FIG. 24 illustrates a first step in utilizing the tissue retraction system 1910 in a dissection procedure. As illustrated in FIG. 24 and described above, the clinician may first advance the support catheter 1970 in a proximal-to-distal direction (relative to the distal end 1928 of the delivery catheter 1926). However, as discussed above, in some examples the pull-back member 1972 may be used in place of the support catheter 1970 to push the tissue retraction device 1922 forward and out the distal end 1928 of the delivery catheter 1926). This forward movement of the support catheter 1970 (or pull-back member 1972) may push the tissue retraction device 1922 forward and out the distal end 1928 of the delivery catheter 1926 FIG. 24 illustrates the tissue retraction device 1922 having been advanced out of the distal end 1928 of the delivery catheter 1926, whereby it is positioned adjacent to the tissue target 1950 (e.g., a cancerous lesion) within lumen 1916. FIG. 24 further illustrates that the pull-back member 1972 may remain engaged to the interface member 1980.

Figure 25:
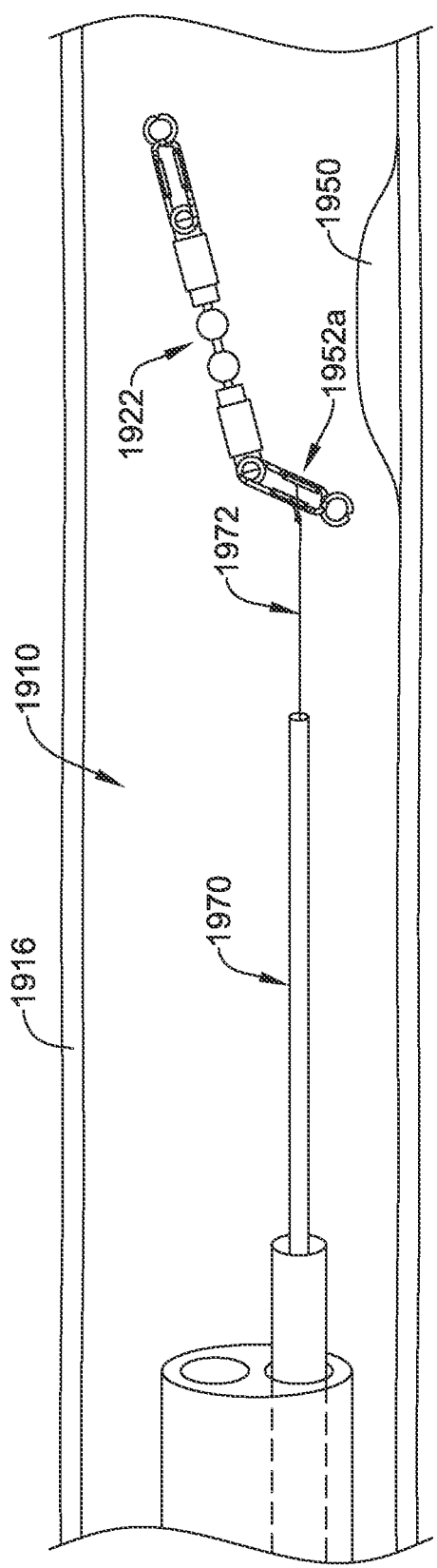

FIG. 25 illustrates an example second step in utilizing the tissue retraction system 1910 in a dissection procedure. FIG. 25 illustrates that a clinician may manipulate the support catheter 1970 to retract the distal end of the support catheter 1970 relative to the pull-back member 1972 the first engagement member 1952a. As illustrated in FIG. 25, retracting the support catheter 1970 may permit the first engagement member 1952a to reposition itself with the lumen of vessel 1916. In other words, retracting support member 1970 may permit the first engagement member 1952a to be positioned at an angle offset from the longitudinal axis of the support catheter 1970 and the pull-back member 1972.

Figure 26:
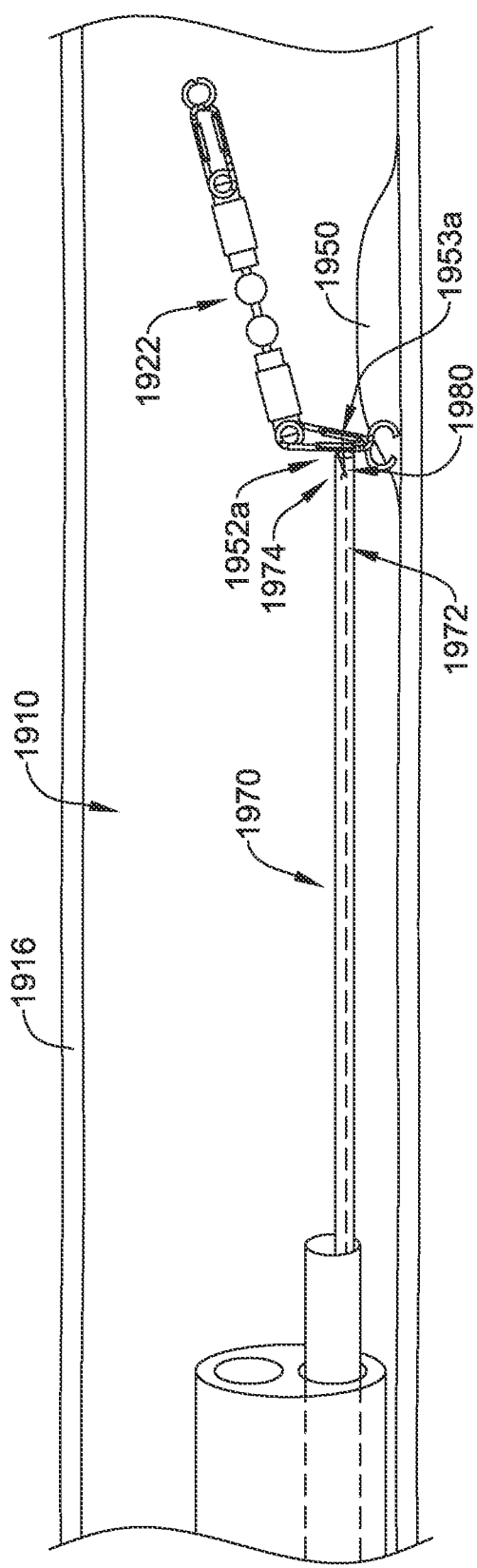

FIG. 26 illustrates an example third step in utilizing the tissue retraction system 1910 in a dissection procedure. FIG. 26 illustrates that a clinician may manipulate the support catheter 1970 and/or the pull-back member 1972 such that the distal end 1974 of the support catheter 1970 is brought into contact with an actuation portion 1953a of the engagement member 1952a. As shown in FIG. 26, the engagement member 1952a may be positioned at approximately a 90 degree angle (e.g., approximately perpendicular) with respect to the distal end 1974 of the support catheter 1970 when the two are in contact. In other words, the longitudinal axis of the engagement member 1952a may be positioned at approximately a 90 degree angle (e.g., approximately perpendicular) with respect to the distal end 1974 of the support catheter 1970 when the two are in contact.

Additionally, once the distal end 1974 of the support catheter 1970 contacts the actuation portion 1953a of the engagement member 1952a, the clinician may withdrawal both the pull-back member 1972 and a portion of the interface member 1980 into the lumen of the support catheter 1970. It can be appreciated that withdrawing the pull-back member 1972 and the interface member 1980 into the lumen of the support catheter may pull the actuation portion 1953a of the first engagement member against the distal end 1974 of the support catheter. Further, pulling the actuation portion 1953a against the distal end 1974 of the support catheter may squeeze the arms of the actuation portion 1953a of the engagement member 1952a together, thereby opening the jaws of the first engagement member. Once opened, the jaws of the engagement member 1952a may be positioned onto the surface of the target tissue 1950. By manipulating the pull-back member 1972 relative to the support catheter 1970 and the first engagement member 1952a, the jaws of the first engagement member 1952a may close and attach the jaws (and, by extension, the first engagement member 1952a) to the surface of target tissue 50. However, it is contemplated that while the example above describes engagement member 1952a as shifting from a closed positioned to an open position, other examples may include the engagement member 1952a shifting from an open position to a closed position.

Figure 27:
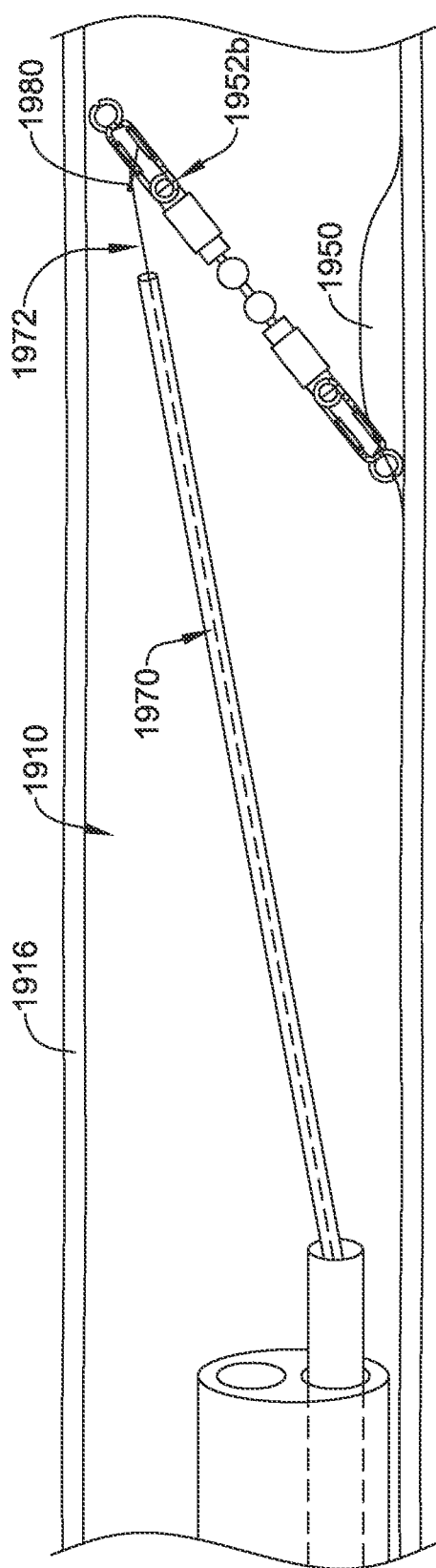

FIG. 27 illustrates an example fourth step in utilizing the tissue retraction system 1910 in a dissection procedure. FIG. 27 shows that the clinician may manipulate the pull-back member 1972 to engage the interface member 1980 coupled to the engagement member 1952b.

Figure 28:
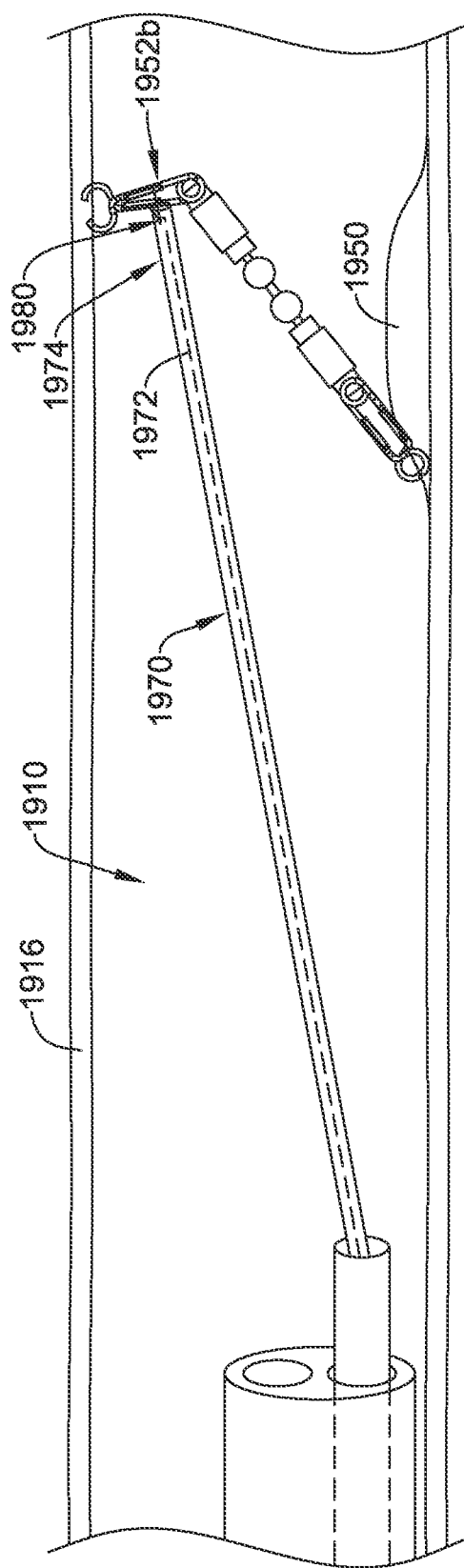

FIG. 28 illustrates an example fifth step in utilizing the tissue retraction system 1910 in a dissection procedure. FIG. 28 illustrates that a clinician may manipulate the support catheter 1970 and/or the pull-back member 1972 such that the distal end 1974 of the support catheter is brought into contact with an actuation portion 1953b of the second engagement member 1952b. As shown in FIG. 26, the engagement member 1952a may be positioned at approximately a 90 degree angle (e.g., approximately perpendicular) with respect to the distal end 1974 of the support catheter 1970 when the two are in contact. In other words, the longitudinal axis of the engagement member 1952a may be positioned at approximately a 90 degree angle (e.g., approximately perpendicular) with respect to the distal end 1974 of the support catheter 1970 when the two are in contact.

Additionally, once the distal end 1974 of the support catheter 1970 is contacting the actuation portion 1953b of the second engagement member 1952b, the clinician may withdrawal both the pull-back member 1972 and a portion of the interface member 1980 into the lumen of the support catheter 1970. It can be appreciated that withdrawing the pull-back member 1972 and the interface member 1980 into the lumen of the support catheter 1970 may pull the actuation portion 1953b of the second engagement member 1952b against the distal end 1974 of the support catheter 1970. Further, pulling the actuation portion 1953b against the distal end 1974 of the support catheter 1970 may squeeze the arms of the actuation portion 1953b of the second engagement member 1952b together, thereby opening the jaws of the second engagement member 1952b. Once opened, the jaws of the second engagement member 1952b may be positioned onto the surface of the body lumen 1916. By manipulating the pull-back member 1972 relative to the support catheter 1970 and the second engagement member 1952b, the jaws of the second engagement member 1952b may close and attach to the surface of target tissue 1950. However, it is contemplated that while the example above describes engagement member 1952a as shifting from a closed positioned to an open position, other examples may include the engagement member 1952a shifting from an open position to a closed position.

Figure 29:
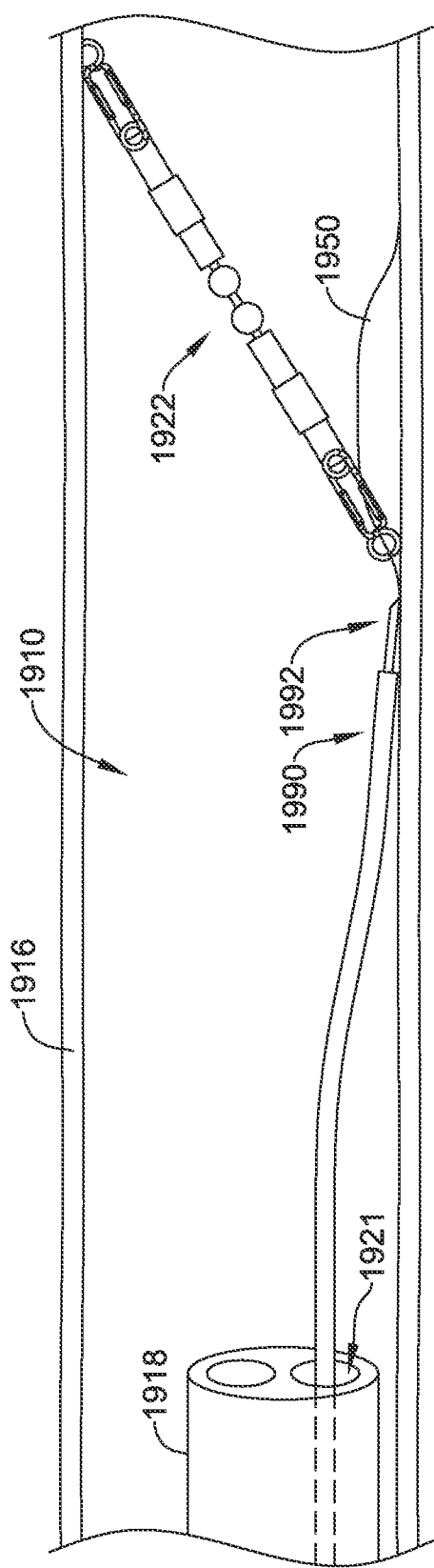

FIG. 29 illustrates an example sixth step in utilizing the tissue retraction system 1910 in a dissection procedure. FIG. 29 illustrates that after the tissue retraction device 1922 has been attached to both the target tissue site 1950 and to the inner surface of the body lumen 1916 at a position spaced away from the target tissue site (which places the tissue retraction device 1922 in tension), the clinician may exchange the support catheter 1970 and the pull-back member 1972 for a cutting tool 1990. The cutting tool 1990 may include a cutting member 1992 positioned at the target tissue 1950. Further, the cutting tool 74 may be advanced within the working channel 1921 of the medical device 1918 as described above. While not shown in the Figures, it can be appreciated that the cutting tool 1992 may be utilized to cut, lift and retract a dissected portion of the target tissue 1950, similar to that described above with respect to FIG. 17.

It should be noted that the features of any of the tissue retraction systems described with respect to particular figures and/or embodiments are not limited to that particular example. Rather, it is contemplated that all of the features or examples disclosed with respect to a single example may be incorporated into any other example disclosed herein.

The materials that can be used for the various components of tissue retraction system 10 and the various devices disclosed herein may include those commonly associated with medical devices. For simplicity purposes, to the extent the following discussion makes reference to tissue retraction system 10, it is not intended to limit the devices and methods described herein only to tissue retraction system 10, as the discussion may be applied to other similar devices disclosed herein.

Tissue retraction system 10 and/or other components of tissue retraction system 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether)phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), styrene ethylene buthylene styrene (SEBS), Thermoplastic Elastomers (TPE) (such as Medalist® available from Teknor Apex and/or Mediprene® available from Hexpol TPE), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of tissue retraction system 10 and/or other components of tissue retraction system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of tissue retraction system 10 and/or other components of tissue retraction system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of tissue retraction system 10 and/or other components of tissue retraction system 10 to achieve the same result.

In some embodiments, a degree of Magnetic Resonance Imaging (MRI) compatibility is imparted into tissue retraction system 10 and/or other components of tissue retraction system 10. For example, tissue retraction system 10 and/or other components of tissue retraction system 10, or portions thereof, may be made of a material that does not substantially distort the image and create substantial artifacts (e.g., gaps in the image). Certain ferromagnetic materials, for example, may not be suitable because they may create artifacts in an MRI image. Tissue retraction system 10 and/or other components of tissue retraction system 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A tissue retraction device, comprising:
   a first engagement member having a first end and a second end;
   a second engagement member having a first end and a second end;
   a first tether disposed between the first engagement member and the second engagement member; and
   an alignment member disposed over the first tether to prevent the first tether from bending or folding;
   wherein at least one of the first engagement member or the second engagement member further includes a pair of gripping members.

2. The tissue retraction device of claim 1, wherein the first tether is elongatable.

3. The tissue retraction device of claim 2, wherein the first tether includes a plurality of markers, wherein the markers are designed to indicate the degree of elongation of the first tether.

4. The tissue retraction device of claim 1, further comprising a second tether disposed between the first engagement member and the second engagement member.

5. The tissue retraction device of claim 4, further comprising a second alignment member disposed over the second tether.

6. The tissue retraction device of claim 5, wherein the second alignment member is disposed over the second tether to prevent the second tether from bending or folding.

7. The tissue retraction device of claim 4, wherein the second tether is elongatable.

8. The tissue retraction device of claim 1, wherein the first tether is elastic.

9. The tissue retraction device of claim 8, further including a second elastic tether.

10. The tissue retraction device of claim 1, wherein the first tether is configured to be stored within the first alignment member.

11. The tissue retraction device of claim 1, wherein the first alignment member is tubular and has sufficient stiffness and column strength to withstand compression.

12. The tissue retraction device of claim 1, wherein the alignment member is stiffer than the first tether.

13. The tissue retraction device of claim 1, wherein the first engagement member and the second engagement member each include a pair of gripping members coupled thereto.

14. The tissue retraction device of claim 1, further comprising a first swivel disposed between the first engagement member and the second engagement member configured to permit the first engagement member to rotate relative to the second engagement member.

15. The tissue retraction device of claim 14, wherein the first swivel is disposed between the first tether and one of the first engagement member or the second engagement member.

16. A tissue retraction system, comprising:
   a tissue retraction device, wherein the tissue retraction device includes:
      a first engagement member having a first end and a second end;
      a second engagement member having a first end and a second end;
      a first tether disposed between the first and second engagement members; and
      a first alignment member disposed over the first tether to prevent the first tether from bending or folding;
   a delivery catheter including a distal end, a proximal end, and a lumen extending therein;
   wherein the tissue retraction device is positioned within the lumen of the delivery catheter prior to being deployed in a body lumen; and
   wherein the alignment member maintains the first tether in a substantially straight orientation within the delivery catheter.

17. A tissue retraction device, comprising:
   a first engagement member having a first end and a second end;
   a second engagement member having a first end and a second end;
   a first tether disposed between the first engagement member and the second engagement member; and
   an alignment member disposed over the first tether to allow the first tether to be stored therein without being entangled with an engagement member during delivery to tissue;
   wherein at least one of the first engagement member or the second engagement member further includes a pair of gripping members.

18. The tissue retraction device of claim 17, wherein the first tether is elongatable.

19. The tissue retraction device of claim 17, wherein the first tether is elastic.

20. The tissue retraction device of claim 17, wherein the first alignment member is tubular and has sufficient stiffness and column strength to withstand compression.

* * * * *